(12) United States Patent
Guarraia et al.

(10) Patent No.: US 10,709,887 B2
(45) Date of Patent: Jul. 14, 2020

(54) DEVICES FOR DELIVERING NON-INVASIVE NEUROMODULATION TO A PATIENT

(71) Applicant: Neurohabilitation Corporation, Newtown, PA (US)

(72) Inventors: Mark Guarraia, Cranston, RI (US); Aidan Petrie, Jamestown, RI (US); Justin Fisk, Providence, RI (US); Adam Muratori, Greenville, RI (US); Jeffrey M. Wallace, Saunderstown, RI (US); Jeffrey C. Morang, Foxborough, MA (US)

(73) Assignee: Helius Medical, Inc, Newtown, PA (US)

( * ) Notice: Subject to any disclaimer, the term of this patent is extended or adjusted under 35 U.S.C. 154(b) by 96 days.

(21) Appl. No.: 16/005,624

(22) Filed: Jun. 11, 2018

(65) Prior Publication Data

US 2018/0289951 A1     Oct. 11, 2018

Related U.S. Application Data

(62) Division of application No. 14/559,045, filed on Dec. 3, 2014, now Pat. No. 9,993,640.

(51) Int. Cl.
    *A61N 1/05*       (2006.01)
    *A61N 1/04*       (2006.01)
    *A61N 1/36*       (2006.01)

(52) U.S. Cl.
    CPC ......... *A61N 1/0548* (2013.01); *A61N 1/0456* (2013.01); *A61N 1/0476* (2013.01);
    (Continued)

(58) Field of Classification Search
    CPC ... A61N 1/0548; A61N 1/0456; A61N 1/0476
    (Continued)

(56) References Cited

U.S. PATENT DOCUMENTS 2,055,540 A    9/1936   Kamofsky
3,851,651 A    12/1974   Icenbice, Jr.
(Continued)

FOREIGN PATENT DOCUMENTS

EP          2671612 A1    12/2013
KR    20110038314 A     4/2011
(Continued)

OTHER PUBLICATIONS

Danilov, Y.P. et al.; "Emerging Noninvasive Neurostimulation Technologies: CN-NINM and SYMPATOCORECTION;" Journal of Behavioral and Brain Science; 2014; 4; pp. 105-113.
(Continued)

*Primary Examiner* — Amanda K Hulbert
*Assistant Examiner* — Philip C Edwards
(74) *Attorney, Agent, or Firm* — Proskauer Rose LLP

(57) ABSTRACT

A mouthpiece for providing non-invasive neuromodulation to a patient. The mouthpiece includes an elongated housing having a center of gravity located within a posterior region, a positioning pad attached to the top surface of the elongated housing for minimizing contact between a patient's upper teeth and the exterior top surface of the elongated housing, and a printed circuit board mounted to a bottom portion of the elongated housing, the printed circuit board having a plurality of electrodes for delivering subcutaneous local electrical stimulation to the patient's tongue. In some embodiments, the mouthpiece includes at least one locator disposed along the anterior region of the elongated housing for contacting a patient's teeth to securely position the mouthpiece within the patient's mouth.

26 Claims, 21 Drawing Sheets

(52) U.S. Cl.
CPC .......... *A61N 1/0484* (2013.01); *A61N 1/0529* (2013.01); *A61N 1/36014* (2013.01); *A61N 1/36025* (2013.01)

(58) Field of Classification Search
USPC ....................................................... 607/134
See application file for complete search history.

(56) References Cited

U.S. PATENT DOCUMENTS

| | | | |
|---|---|---|---|
| 4,865,048 A | 9/1989 | Eckerson | |
| 4,924,880 A | 5/1990 | O'Neill et al. | |
| 4,995,404 A | 2/1991 | Nemir | |
| 5,259,762 A | 11/1993 | Farrell | |
| 5,265,624 A | 11/1993 | Bowman | |
| 5,269,303 A | 12/1993 | Wernicke et al. | |
| 5,299,569 A | 4/1994 | Wernicke et al. | |
| 5,540,734 A | 7/1996 | Zabara | |
| 5,553,626 A | 9/1996 | Burger et al. | |
| 5,792,067 A | 8/1998 | Karell | |
| 5,794,621 A | 8/1998 | Hogan et al. | |
| 5,878,154 A | 3/1999 | Schimmelpfennig | |
| D409,307 S | 5/1999 | Phleps et al. | |
| 6,066,163 A | 5/2000 | John | |
| 6,089,864 A | 7/2000 | Buckner et al. | |
| 6,161,044 A | 12/2000 | Silverstone | |
| D437,058 S | 1/2001 | Gozani | |
| 6,169,781 B1 | 1/2001 | Doebert et al. | |
| 6,267,733 B1 | 7/2001 | Peterson et al. | |
| D449,376 S | 10/2001 | McDonald et al. | |
| D449,883 S | 10/2001 | McDonald et al. | |
| D451,598 S | 12/2001 | McDonald et al. | |
| 6,326,901 B1 | 12/2001 | Gonzales | |
| 6,339,725 B1 | 1/2002 | Naritoku et al. | |
| 6,366,813 B1 | 4/2002 | DiLorenzo | |
| 6,366,814 B1 | 4/2002 | Boveja et al. | |
| 6,405,079 B1 | 6/2002 | Ansarinia | |
| 6,430,450 B1* | 8/2002 | Bach-y-Rita | A61F 9/08 379/52 |
| D462,357 S | 9/2002 | Jenkins | |
| 6,463,328 B1 | 10/2002 | John | |
| 6,526,318 B1 | 2/2003 | Ansarinia | |
| 6,546,291 B2 | 4/2003 | Merteld et al. | |
| 6,556,868 B2 | 4/2003 | Naritoku et al. | |
| 6,954,668 B1 | 10/2005 | Cuozzo | |
| D515,697 S | 2/2006 | Nakamura et al. | |
| D531,314 S | 10/2006 | Atkinson et al. | |
| D542,408 S | 5/2007 | Oldenburg et al. | |
| 7,228,178 B2 | 6/2007 | Carroll et al. | |
| 7,236,830 B2 | 6/2007 | Gliner | |
| D555,252 S | 11/2007 | Kitayama et al. | |
| D557,685 S | 12/2007 | Lee | |
| 7,333,020 B2 | 2/2008 | Cohen et al. | |
| D565,184 S | 3/2008 | Royzen | |
| D575,268 S | 8/2008 | Christopher et al. | |
| D578,222 S | 10/2008 | Sakurai et al. | |
| D579,552 S | 10/2008 | Oldenburg et al. | |
| 7,483,747 B2 | 1/2009 | Gliner et al. | |
| D593,067 S | 5/2009 | Millora et al. | |
| 7,563,929 B2 | 7/2009 | Hobbs et al. | |
| 7,565,200 B2 | 7/2009 | Wyler et al. | |
| 7,640,062 B2 | 12/2009 | Shalev | |
| 7,672,730 B2 | 3/2010 | Firlik et al. | |
| 7,725,192 B2 | 5/2010 | Eskandar et al. | |
| D617,308 S | 6/2010 | Nousiainen et al. | |
| 7,747,325 B2 | 6/2010 | Dilorenzo | |
| 7,768,499 B2 | 8/2010 | Sturtz | |
| D624,189 S | 9/2010 | Rutt et al. | |
| D663,714 S | 7/2012 | Kang et al. | |
| D669,881 S | 10/2012 | Clements et al. | |
| 8,290,582 B2 | 10/2012 | Lin et al. | |
| D687,018 S | 7/2013 | Afshar | |
| D706,745 S | 6/2014 | Nakagawa | |
| D707,199 S | 6/2014 | Cepress et al. | |
| D709,673 S | 7/2014 | Aimone et al. | |
| D710,718 S | 8/2014 | Ichihashi et al. | |
| 8,805,548 B2 | 8/2014 | Mignolet et al. | |
| D713,531 S | 9/2014 | Way et al. | |
| 8,849,407 B1 | 9/2014 | Danilov et al. | |
| D716,759 S | 11/2014 | Ha et al. | |
| D721,673 S | 1/2015 | Park et al. | |
| D723,510 S | 3/2015 | Ishikura | |
| D724,197 S | 3/2015 | Hughes | |
| D725,262 S | 3/2015 | Chowdhury | |
| D728,109 S | 4/2015 | Ko | |
| D730,867 S | 6/2015 | Park et al. | |
| D731,999 S | 6/2015 | Cepress et al. | |
| D739,122 S | 9/2015 | Aimone et al. | |
| 9,124,979 B2 | 9/2015 | O'Grady et al. | |
| D744,658 S | 12/2015 | Hilkey-Boyatt | |
| 9,993,641 B2 | 6/2018 | Williams et al. | |
| 2003/0220677 A1 | 11/2003 | Doan et al. | |
| 2004/0073270 A1 | 4/2004 | Firlik et al. | |
| 2004/0073271 A1 | 4/2004 | Harry et al. | |
| 2005/0089829 A1 | 4/2005 | Wasowicz | |
| 2005/0197529 A1 | 9/2005 | Hoshihara et al. | |
| 2005/0203582 A1 | 9/2005 | Healy et al. | |
| 2005/0240253 A1 | 10/2005 | Tyler et al. | |
| 2006/0161218 A1 | 7/2006 | Danilov | |
| 2006/0241718 A1 | 10/2006 | Tyler et al. | |
| 2007/0248238 A1 | 10/2007 | Abreu | |
| 2007/0250119 A1 | 10/2007 | Tyler et al. | |
| 2007/0293917 A1 | 12/2007 | Thompson et al. | |
| 2007/0293918 A1 | 12/2007 | Thompson et al. | |
| 2008/0009772 A1 | 1/2008 | Tyler et al. | |
| 2008/0027510 A1 | 1/2008 | McClure et al. | |
| 2008/0082131 A1 | 4/2008 | Llanos | |
| 2008/0208287 A1 | 8/2008 | Palermo et al. | |
| 2008/0222670 A1 | 9/2008 | Lee et al. | |
| 2008/0228239 A1 | 9/2008 | Tyler et al. | |
| 2008/0233541 A1 | 9/2008 | De Vreese et al. | |
| 2008/0234604 A1 | 9/2008 | Burgmans | |
| 2008/0281550 A1 | 11/2008 | Hogle et al. | |
| 2009/0048647 A1 | 2/2009 | Tingey | |
| 2009/0082831 A1 | 3/2009 | Paul et al. | |
| 2009/0082839 A1 | 3/2009 | Lindquist et al. | |
| 2009/0312808 A1 | 12/2009 | Tyler et al. | |
| 2009/0312817 A1 | 12/2009 | Hogle et al. | |
| 2009/0326604 A1 | 12/2009 | Tyler et al. | |
| 2011/0093036 A1 | 4/2011 | Mashiach | |
| 2011/0125184 A1 | 5/2011 | Allen | |
| 2011/0201944 A1 | 8/2011 | Higgins et al. | |
| 2012/0010672 A1 | 1/2012 | Crespi | |
| 2012/0123225 A1 | 5/2012 | Al-Tawil | |
| 2012/0165862 A1 | 6/2012 | Allen | |
| 2013/0096641 A1 | 4/2013 | Strother et al. | |
| 2013/0256345 A1 | 10/2013 | Larkin | |
| 2013/0273490 A1 | 10/2013 | Way et al. | |
| 2014/0039579 A1 | 2/2014 | Mashiach et al. | |
| 2014/0135868 A1 | 5/2014 | Bashyam | |
| 2014/0172041 A1 | 6/2014 | Draghici et al. | |
| 2014/0194946 A1 | 7/2014 | Thomas et al. | |
| 2014/0379049 A1 | 12/2014 | Mashiach et al. | |
| 2015/0057719 A1 | 2/2015 | Tang | |
| 2015/0264474 A1 | 9/2015 | Seo et al. | |

FOREIGN PATENT DOCUMENTS

| | | |
|---|---|---|
| RU | 2215558 C2 | 11/2003 |
| RU | 2248227 C1 | 3/2005 |
| SU | 1068128 A1 | 1/1984 |
| WO | 02066111 A1 | 8/2002 |
| WO | 2014150090 A1 | 9/2014 |

OTHER PUBLICATIONS

Hamilton; "Impact of Acoustic and Tactile Multi-Modal Stimulation on Objective and Subjective Measures of Permanent Intractable Tinnitus: A Prospective Research Study;" Hamilton Institute; National University of Ireland Maynooth; Jun. 2014; 141 pages.
Helius Medical Technologies, Inc.; "Interchange PoNS Unit; Listing Statement; Form 2A;" Jun. 20, 2014; http://www.cnsx.ca/

(56) References Cited

OTHER PUBLICATIONS cmsAssets/docs/Filings/2014/2014_06_20_20_39_31_HSM_Helius_Form_2A_Listing_Statement.pdf; Nov. 16, 2015; 3 pages.

Helius Medical Technologies, Inc.; "The PoNS Device;" 2015; http://www.heliusmedical.com/divisions/neurohabilitation/pons-device; retrieved on Dec. 2, 2015; 4 pages.

Tyler, M.E, et al., "Non-invasive Neuromodulation to improve gait in chronic multiple sclerosis: a randomized double blind controlled pilot trial," Journal of Neuroengineering and Rehabilitation, 2014, pp. 1-10.

US Army; "Mouth Device in Clinical Trials as Possible Treatment for TBI;" Feb. 14, 2013; http://www.army.mil/article/96521/Mouth_device-in_clinical_trials_as_possible_treatment_for_TBI; retrieved on Feb. 2, 2015; 2 pages.

Sidyakina I.V.; "Swallowing rehabilitation of patients with serious diseases and brain injuries;" Restorative Medicine Bulletin; No. 4; 2011; pp. 14-17.

\* cited by examiner

US 10,709,887 B2

DEVICES FOR DELIVERING NON-INVASIVE NEUROMODULATION TO A PATIENT

CROSS REFERENCE TO RELATED APPLICATION

This application is a division of U.S. application Ser. No. 14/559,045, filed Dec. 3, 2014, now U.S. Pat. No. 9,993,640, which is incorporated by reference herein in its entirety.

FIELD OF THE INVENTION

In general, the invention relates to devices and methods for non-invasive neurostimulation of a subject's brain. More specifically, the invention relates to devices and methods for non-invasive neurostimulation of a subject's brain to effect treatment of various maladies.

BACKGROUND OF THE INVENTION

Traumatic brain injury (TBI) is a leading cause of disability around the world. Each year in the United States, about two million people suffer a TBI, with many suffering long term symptoms. Long term symptoms can include impaired attention, impaired judgment, reduced processing speed, and defects in abstract reasoning, planning, problem-solving and multitasking.

A stroke is a loss of brain function due to a disturbance in the blood supply to the brain. Every year, about 800,000 people in the United States will have a stroke. Stroke is a leading cause of long-term disability in the United States, with nearly half of older stroke survivors experiencing moderate to severe disability. Long term effects can include seizures, incontinence, vision disturbance or loss of vision, dysphagia, pain, fatigue, loss of cognitive function, aphasia, loss of short-term and/or long-term memory, and depression.

Multiple sclerosis (MS) is a disease that causes damage to the nerve cells in the brain and spinal cord. Globally, there are about 2.5 million people who suffer from MS. Symptoms can vary greatly depending on the specific location of the damaged portion of the brain or spinal cord. Symptoms include hypoesthesia, difficulties with coordination and balance, dysarthria, dysphagia, nystagmus, bladder and bowel difficulties, cognitive impairment and major depression to name a few.

Alzheimer's disease (AD) is a neurodegenerative disorder affecting over 25 million people worldwide. Symptoms of AD include confusion, irritability, aggression, mood swings, trouble with language, and both short and long term memory loss. In developed countries, AD is one of the most costly diseases to society.

Parkinson's disease (PD) is a degenerative disorder of the central nervous system, affecting more than 7 million people globally. Symptoms of PD include tremor, bradykinesia, rigidity, postural instability, cognitive disturbances, and behavior and mood alterations.

One approach to treating the long term symptoms associated with TBI, stroke, MS, AD, and PD is neurorehabilitation. Neurorehabilitation involves processes designed to help patients recover from nervous system injuries. Traditionally, neurorehabilitation involves physical therapy (e.g., balance retraining), occupational therapy (e.g., safety training, cognitive retraining for memory), psychological therapy, speech and language therapy, and therapies focused on daily function and community re-integration.

Another approach to treating the long term symptoms associated with TBI, stroke, MS, AD, and PD is neurostimulation. Neurostimulation is a therapeutic activation of part of the nervous system. For example, activation of the nervous system can be achieved through electrical stimulation, magnetic stimulation, or mechanical stimulation. Typical approaches focused mainly on invasive techniques, such as deep brain stimulation (DBS), spinal cord stimulation (SCS), cochlear implants, visual prosthesis, and cardiac electrostimulation devices. Only recently have non-invasive approaches to neurostimulation become more mainstream.

Despite many advances in the areas of neurorehabilitation and neurostimulation, there exists an urgent need for treatments that employ a combined approach, including both neurorehabilitation and neurostimulation to improve the recovery of patients having TBI, stroke, multiple sclerosis, Alzheimer's, Parkinson's, depression, memory loss, compulsive behavior, or any other neurological impairment.

SUMMARY OF THE INVENTION

The invention, in various embodiments, features methods and devices for combining non-invasive neuromodulation with traditional neurorehabilitation therapies. Clinical studies have shown that methods combining neurostimulation with neurorehabilitation are effective in treating the long term neurological impairments due to a range of maladies such as TBI, stroke, MS, AD, and PD.

In one aspect, the invention features a mouthpiece for providing non-invasive neuromodulation to a patient. The mouthpiece includes an elongated housing having an anterior region and a posterior region, the elongated housing having a non-planar exterior top surface and a center of gravity located within the posterior region, the posterior region of the elongated housing having a volume greater than an anterior region of the elongated housing. The mouthpiece also includes a positioning pad attached to the top surface of the housing for minimizing contact between a patient's upper teeth and the exterior top surface of the elongated housing. The mouthpiece also includes a printed circuit board mounted to a bottom portion of the elongated housing, the printed circuit board having a plurality of electrodes for delivering subcutaneous local electrical stimulation to the patient's tongue.

In some embodiments, the mouthpiece includes an elongated housing with a posterior region having an average width greater than an anterior region of the elongated housing. In some embodiments, the mouthpiece includes an elongated housing with a posterior region having an average height greater than an anterior region of the elongated housing. In some embodiments, the mouthpiece includes an elongated housing with an anterior region having a length greater than a posterior region of the elongated housing. In some embodiments, the mouthpiece includes an elongated housing having an average length greater than an average width and an average height. In some embodiments, the mouthpiece includes an elongated housing having an average width greater than an average height. In some embodiments, the mouthpiece includes an elongated housing with a posterior region having an average density greater than an anterior region of the elongated housing. In some embodiments, the mouthpiece includes an elongated housing with a posterior region having a first average width and with an anterior region having a second average width, the elongated housing having a horizontal transition region connecting the anterior region to the posterior region, the horizontal transition region having a width that varies smoothly between the first width and the second width. In some embodiments, the width of the horizontal transition region varies linearly between the first width and the second width. In some embodiments, the mouthpiece includes an elongated housing with a posterior region having a first average height and with an anterior region having a second average height, the elongated housing having a vertical transition region connecting the anterior region to the posterior region, the vertical transition region having a height that varies smoothly between the first average height and the second average height. In some embodiments, the height of the vertical transition region varies linearly between the first height and the second height. In some embodiments, the width of the horizontal transition region has a concave profile. In some embodiments, the posterior region has a convex shape. In some embodiments, the mouthpiece includes an elongated housing with a posterior region having a first average width and with an anterior region having a second average width, the elongated housing having a horizontal transition region connecting the anterior region to the posterior region, the horizontal transition region having a width that varies linearly between the first average width and the second average width and an elongated housing with a posterior region having a first average height and with an anterior region having a second average height, the elongated housing having a vertical transition region connecting the anterior region to the posterior region, the vertical transition region having a height that varies smoothly between the first average height and the second average height. In some embodiments, the anterior region of the elongated housing includes a first plateau having a first height surrounded by a second plateau having a second height. In some embodiments, the first height is greater than the second height. In some embodiments, the anterior region of the elongated housing includes a first plateau having a first height surrounded by a second plateau having a second height. In some embodiments, the first plateau has an ovular shape. In some embodiments, the second height is smaller than the first height. In some embodiments, the posterior region of the elongated housing includes a rectangular shaped plateau. In some embodiments, the mouthpiece includes an elongated housing with a posterior region having a maximum width greater than an anterior region of the elongated housing. In some embodiments, the mouthpiece includes an elongated housing with a posterior region having a maximum height greater than an anterior region of the elongated housing. In some embodiments, the mouthpiece includes an elongated housing with a posterior region having a minimum width greater than a maximum width of an anterior region of the elongated housing. In some embodiments, the mouthpiece includes an elongated housing with a posterior region having a minimum height greater than a maximum height of an anterior region of the elongated housing. In some embodiments, the mouthpiece includes an elongated housing having a posterior region with a greater mass than an anterior region. In some embodiments, a portion of the anterior region is removed to cause the anterior region to have a smaller mass than the posterior region. In some embodiments, a mass is added to the posterior region to cause the posterior region to have a larger mass than the anterior region.

In another aspect, the invention features a mouthpiece for providing non-invasive neuromodulation to a patient. The mouthpiece includes an elongated housing having an anterior region and a posterior region, the elongated housing having a non-planar exterior top surface and a center of gravity located within the posterior region. The mouthpiece also includes a positioning pad attached to the top surface of the housing for minimizing contact between a patient's upper teeth and the exterior top surface of the elongated housing. The mouthpiece also includes a printed circuit board mounted to a bottom portion of the elongated housing, the printed circuit board having a plurality of electrodes for delivering subcutaneous local electrical stimulation to the patient's tongue.

In some embodiments, the mouthpiece includes an elongated housing having a posterior region with a greater mass than an anterior region. In some embodiments, a portion of the anterior region is removed to cause the anterior region to have a smaller mass than the posterior region. In some embodiments, a mass is added to the posterior region to cause the posterior region to have a larger mass than the anterior region.

In another aspect, the invention features a mouthpiece for providing non-invasive neuromodulation to a patient. The mouthpiece includes an elongated housing having an anterior region and a posterior region, the elongated housing having a non-planar exterior top surface and a center of gravity located within the posterior region, the posterior region of the elongated housing having a volume greater than an anterior region of the elongated housing. The mouthpiece also includes a printed circuit board mounted to a bottom portion of the elongated housing, the printed circuit board having a plurality of electrodes for delivering subcutaneous local electrical stimulation to the patient's tongue.

In another aspect, the invention features a method of placing a mouthpiece in a patient's mouth prior to engaging in a non-invasive neuromodulation therapy session. The method involves providing a mouthpiece having locators to the patient. The method also involves placing the mouthpiece in the patient's mouth. The method also involves manually adjusting the mouthpiece until the locators are in contact with the patient's anatomy.

In some embodiments, the method involves manually adjusting the mouthpiece until at least one locator is in contact with the tip of the patient's tongue. In some embodiments, the method involves manually adjusting the mouthpiece until at least one locator is in contact with the patient's lips. In some embodiments, the method involves manually adjusting the mouthpiece until at least one locator is in contact with the patient's teeth.

In another aspect, the invention features a mouthpiece for providing non-invasive neuromodulation to a patient. The mouthpiece includes an elongated housing having an anterior region and a posterior region, the elongated housing having a non-planar exterior top surface. The mouthpiece also includes a positioning pad, having an anterior and a posterior region, the positioning pad attached to the top surface of the housing for minimizing contact between a patient's upper teeth and the exterior top surface of the elongated housing. The mouthpiece also includes a first locator disposed along the anterior region of the elongated housing integral with the top surface, the first locator contacting a patient's upper teeth to securely position the mouthpiece within the patient's mouth. The mouthpiece also includes a printed circuit board mounted to a bottom portion of the elongated housing, the printed circuit board having a plurality of electrodes for delivering subcutaneous local electrical stimulation to the patient's tongue.

In some embodiments, the locator comprises an inverted trench, a trench, or a step. In some embodiments, the mouthpiece includes a second locator traversing an anterior region of the printed circuit board, the second locator mechanically coupling to a patient's lower teeth to secure a position of the mouthpiece within the patient's mouth. In some embodiments, the second locator comprises an inverted trench, a trench, a contour or a step. In some embodiments, the elongated housing comprises a plastic material having a hardness of shore 90A. In some embodiments, the positioning pad comprises a biocompatible material having a hardness of shore 30A. In some embodiments, the first locator prevents the posterior region of the elongated housing, the posterior region of the positioning pad, and the posterior region of the printed circuit board from contacting the patient's tonsils, throat, and circumvallate papillae. In some embodiments, the patient's upper teeth and lower teeth comprise at least one of a patient's central incisors, lateral incisors, or canines.

In another aspect, the invention features a mouthpiece for providing non-invasive neuromodulation to a patient. The mouthpiece includes an elongated housing having an anterior region and a posterior region, the elongated housing having a non-planar exterior top surface. The mouthpiece also includes a positioning pad attached to the top surface of the housing for minimizing contact between a patient's upper teeth and the non-planar exterior top surface of the elongated housing. The mouthpiece also includes a first locator disposed along an anterior region of the positioning pad, the first locator integral with a top surface of the positioning pad and engaging the patient's upper teeth to securely position the mouthpiece within the patient's mouth. The mouthpiece also includes a printed circuit board mounted to a bottom portion of the elongated housing, the printed circuit board having a plurality of electrodes for delivering subcutaneous local electrical stimulation to the patient's tongue.

In some embodiments, the first locator comprises an inverted trench, a trench, a contour or a step. In some embodiments, the mouthpiece includes a second locator traversing an anterior region of the printed circuit board, the second locator mechanically coupling to a patient's lower teeth to secure a position of the mouthpiece within the patient's mouth. In some embodiments, the second locator comprises a trench, an inverted trench, a contour or a step. In some embodiments, the elongated housing comprises a plastic material having a hardness of shore 90A. In some embodiments, the positioning pad comprises a biocompatible material having a hardness of shore 30A. In some embodiments, the locator prevents the posterior region of the elongated housing, the posterior region of the positioning pad, and the posterior region of the printed circuit board from contacting the patient's tonsils, throat, and circumvallate papillae. In some embodiments, the patient's upper teeth and lower teeth comprise at least one of a patient's central incisors, lateral incisors, or canines.

In another aspect, the invention features a mouthpiece for providing non-invasive neuromodulation to a patient. The mouthpiece includes an elongated housing having an anterior region and a posterior region, the elongated housing having a non-planar exterior top surface. The mouthpiece also includes a positioning pad attached to the top surface of the housing for minimizing contact between a patient's upper teeth and the non-planar exterior top surface of the elongated housing. The mouthpiece also includes a first locator disposed along an anterior region of the mouthpiece, the first locator defining a position of the mouthpiece within the patient's mouth. The mouthpiece also includes a printed circuit board mounted to a bottom portion of the elongated housing, the printed circuit board having a plurality of electrodes for delivering subcutaneous local electrical stimulation to the patient's tongue.

In another aspect, the invention features a mouthpiece for providing non-invasive neuromodulation to a patient. The mouthpiece includes an elongated housing having an anterior region and a posterior region, the elongated housing having a non-planar exterior top surface. The mouthpiece also includes a positioning pad attached to the top surface of the housing for minimizing contact between a patient's upper teeth and the exterior top surface of the elongated housing. The mouthpiece also includes a printed circuit board mounted to a bottom portion of the elongated housing, the printed circuit board having a plurality of electrodes for delivering subcutaneous local electrical stimulation to the patient's tongue.

In some embodiments, the mouthpiece includes an elongated housing with a posterior region having an average width greater than an anterior region of the elongated housing. In some embodiments, the mouthpiece includes an elongated housing with a posterior region having an average height greater than an anterior region of the elongated housing. In some embodiments, the mouthpiece includes an elongated housing with an anterior region having a length greater than a posterior region of the elongated housing. In some embodiments, the mouthpiece includes an elongated housing having an average length greater than an average width and an average height. In some embodiments, the mouthpiece includes an elongated housing having an average width greater than an average height. In some embodiments, the mouthpiece includes an elongated housing with a posterior region having an average density greater than an anterior region of the elongated housing. In some embodiments, the mouthpiece includes an elongated housing with a posterior region having a first average width and with an anterior region having a second average width, the elongated housing having a horizontal transition region connecting the anterior region to the posterior region, the horizontal transition region having a width that varies smoothly between the first width and the second width. In some embodiments, the width of the horizontal transition region varies linearly between the first width and the second width. In some embodiments, the mouthpiece includes an elongated housing with a posterior region having a first average height and with an anterior region having a second average height, the elongated housing having a vertical transition region connecting the anterior region to the posterior region, the vertical transition region having a height that varies smoothly between the first average height and the second average height. In some embodiments, the height of the vertical transition region varies linearly between the first height and the second height. In some embodiments, the width of the horizontal transition region has a concave profile. In some embodiments, the posterior region has a convex shape. In some embodiments, the mouthpiece includes an elongated housing with a posterior region having a first average width and with an anterior region having a second average width, the elongated housing having a horizontal transition region connecting the anterior region to the posterior region, the horizontal transition region having a width that varies linearly between the first average width and the second average width and an elongated housing with a posterior region having a first average height and with an anterior region having a second average height, the elongated housing having a vertical transition region connecting the anterior region to the posterior region, the vertical transition region having a height that varies smoothly between the first average height and the second average height. In some embodiments, the anterior region of the elongated housing includes a first plateau having a first height surrounded by a second plateau having a second height. In some embodiments, the first height is greater than the second height. In some embodiments, the anterior region of the elongated housing includes a first plateau having a first height surrounded by a second plateau having a second height. In some embodiments, the first plateau has an ovular shape. In some embodiments, the second height is smaller than the first height. In some embodiments, the posterior region of the elongated housing includes a rectangular shaped plateau. In some embodiments, the mouthpiece includes an elongated housing with a posterior region having a maximum width greater than an anterior region of the elongated housing. In some embodiments, the mouthpiece includes an elongated housing with a posterior region having a maximum height greater than an anterior region of the elongated housing. In some embodiments, the mouthpiece includes an elongated housing with a posterior region having a minimum width greater than a maximum width of an anterior region of the elongated housing. In some embodiments, the mouthpiece includes an elongated housing with a posterior region having a minimum height greater than a maximum height of an anterior region of the elongated housing. In some embodiments, the mouthpiece includes an elongated housing having a posterior region with a greater mass than an anterior region. In some embodiments, a portion of the anterior region is removed to cause the anterior region to have a smaller mass than the posterior region. In some embodiments, a mass is added to the posterior region to cause the posterior region to have a larger mass than the anterior region.

As used herein, the terms "approximately," "roughly," and "substantially" mean±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

DETAILED DESCRIPTION

Figure 1:
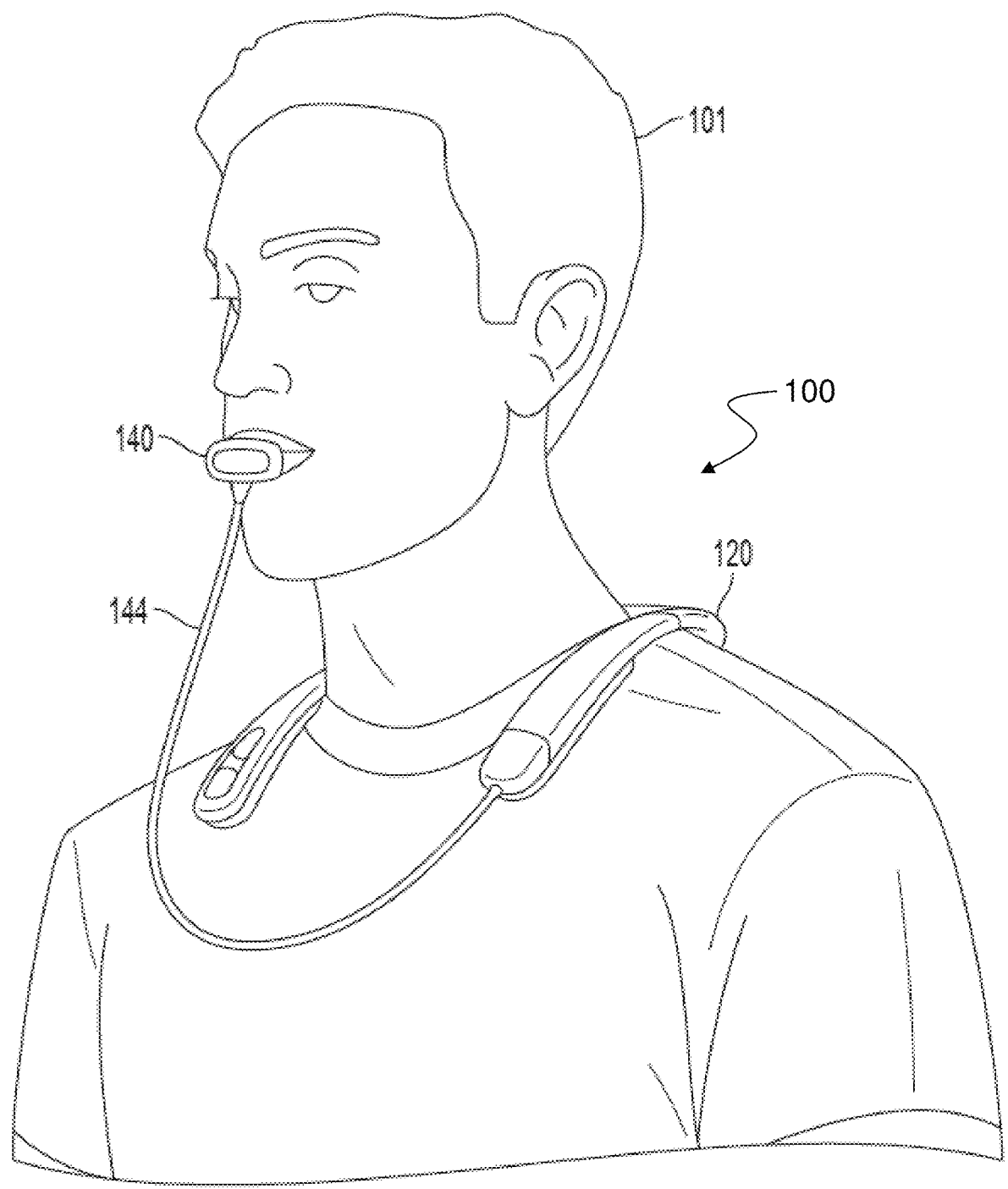
FIG. 1 is a drawing of a patient engaged in a non-invasive neurostimulation therapy session according to an illustrative embodiment of the invention.

FIG. 1 shows a patient 101 undergoing non-invasive neuromodulation therapy (NINM) using a neurostimulation system 100. During a therapy session, the neurostimulation system 100 non-invasively stimulates various nerves located within the patient's oral cavity, including at least one of the trigeminal and facial nerves. In combination with the NINM, the patient engages in an exercise or other activity specifically designed to assist in the neurorehabilitation of the patient. For example, the patient can perform a physical therapy routine (e.g., moving an affected limb, or walking on a treadmill) engage in a mental therapy (e.g., meditation or breathing exercises), or a cognitive exercise (e.g., computer assisted memory exercises) during the application of NINM. The combination of NINM with an appropriately chosen exercise or activity has been shown to be useful in treating a range of maladies including, for example, traumatic brain injury, stroke (TBI), multiple sclerosis (MS), balance, gait, vestibular disorders, visual deficiencies, tremor, headache, migraines, neuropathic pain, hearing loss, speech recognition, auditory problems, speech therapy, cerebral palsy, blood pressure, relaxation, and heart rate. For example, a useful non-invasive neuromodulation (NINM) therapy routine has been recently developed as described in U.S. Pat. No. 8,849,407, the entirety of which is incorporated herein by reference.

Figure 2A:
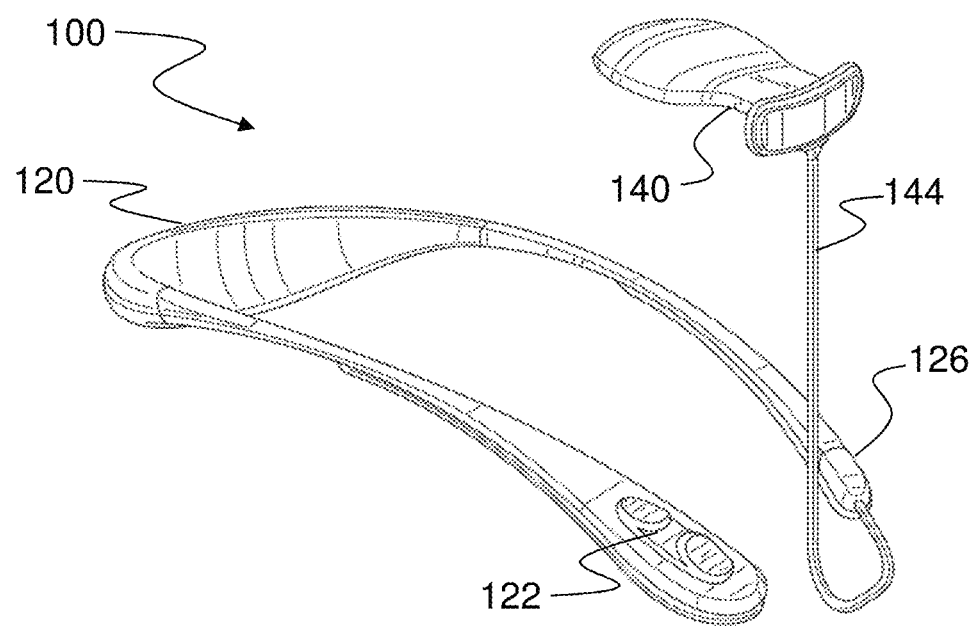
FIGS. 2A and 2B are diagrams showing a neurostimulation system according to an illustrative embodiment of the invention.
Figure 2B:
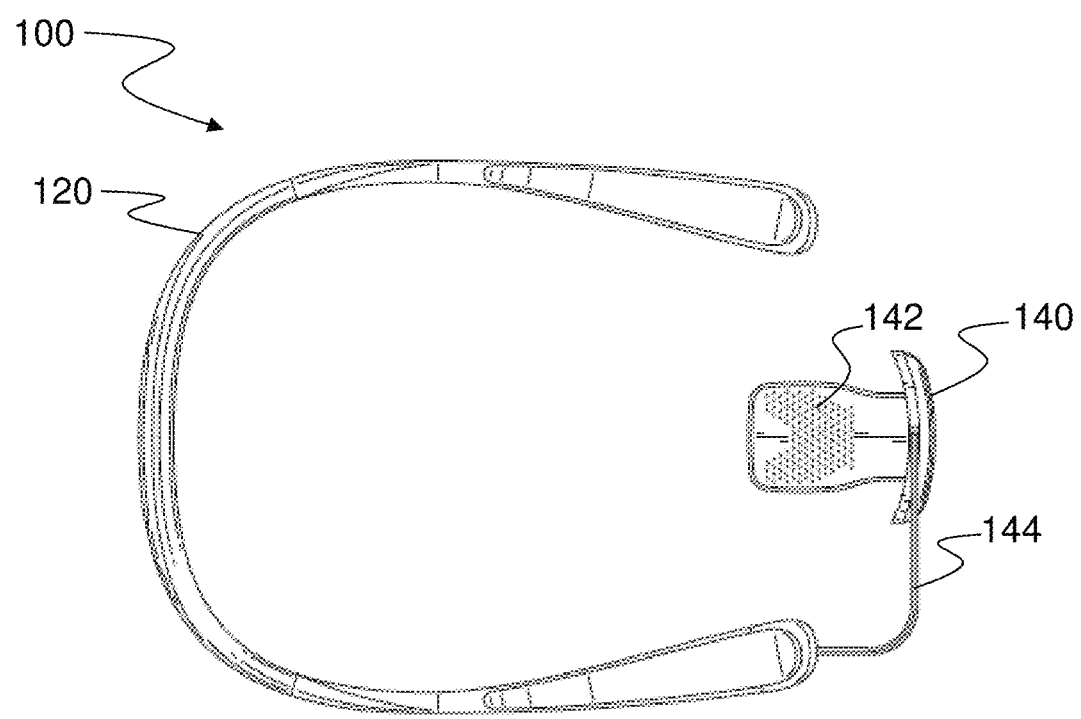
Figure 9A:
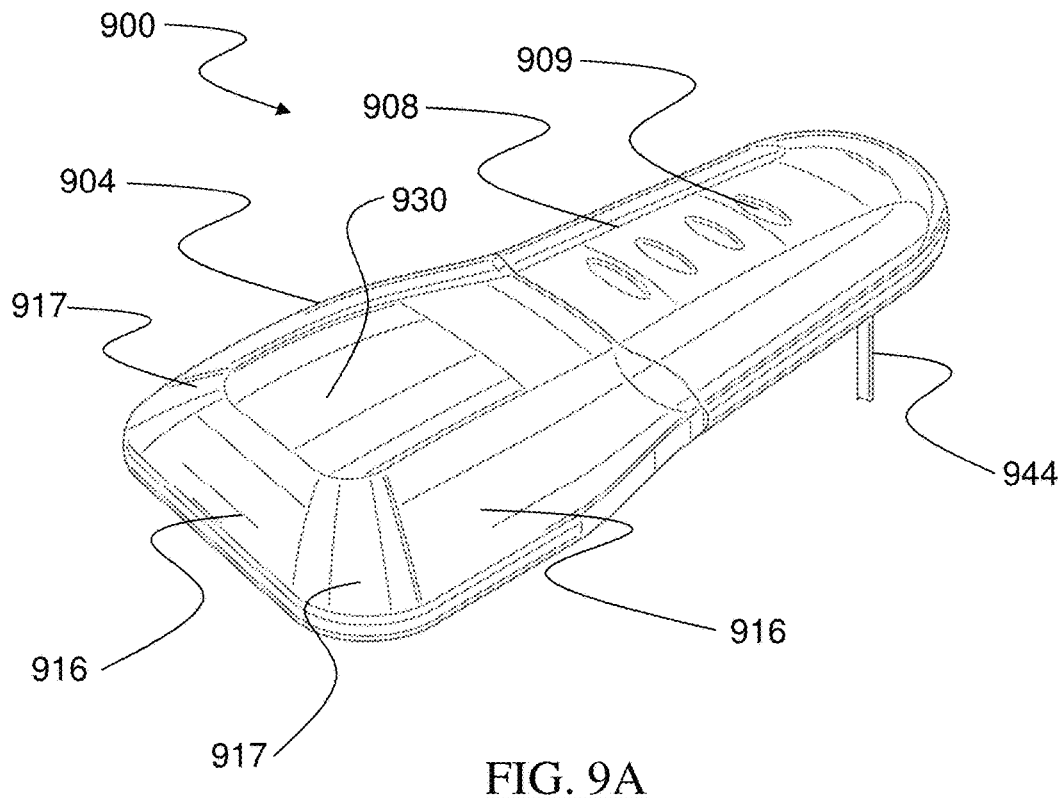
FIG. 9A is a diagram showing an isometric view of a mouthpiece in accordance with an illustrative embodiment of the invention.
Figure 9B:
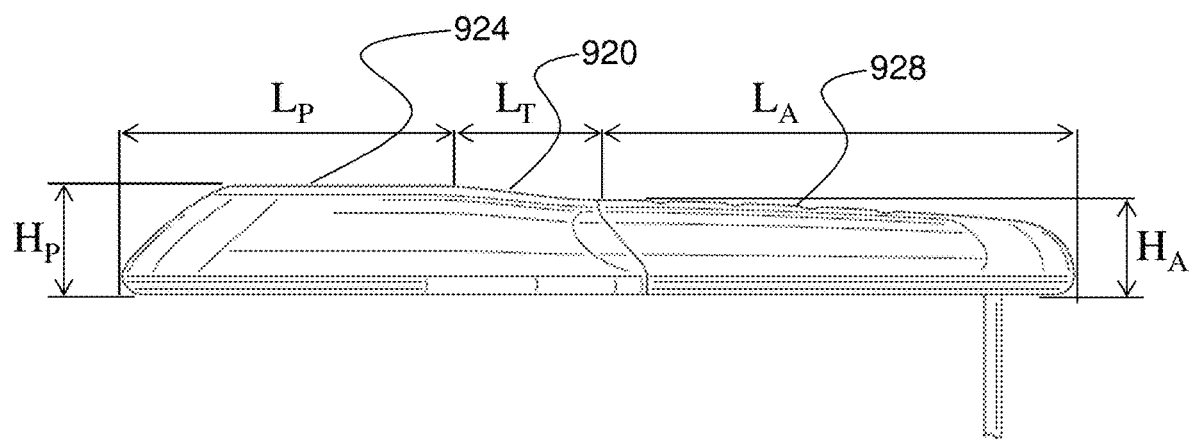
FIG. 9B is a diagram showing a side view of a mouthpiece in accordance with an illustrative embodiment of the invention.
Figure 9C:
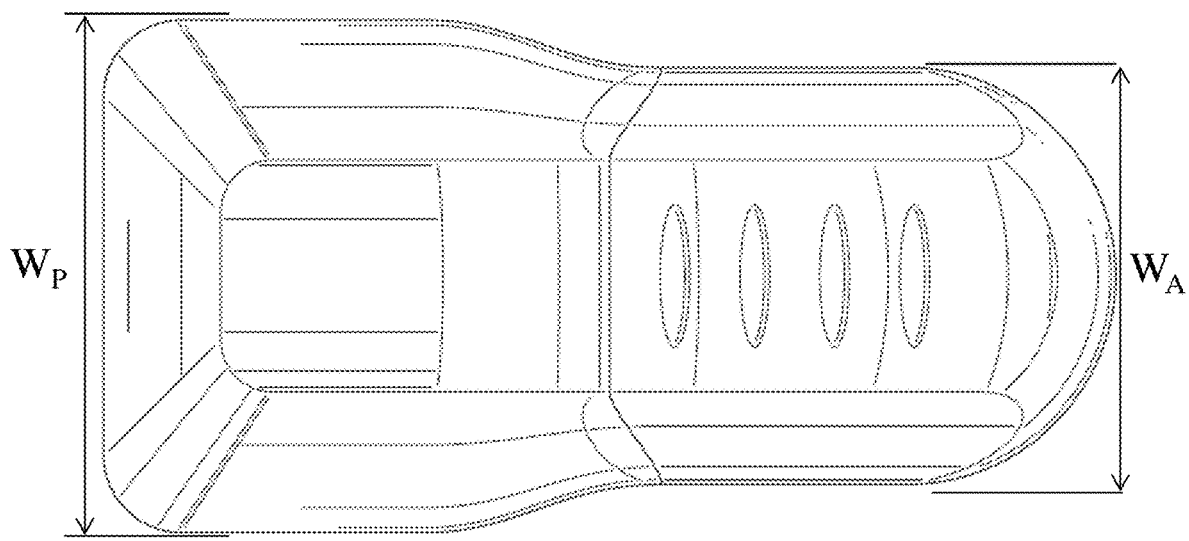
FIG. 9C is a diagram showing a top view of a mouthpiece in accordance with an illustrative embodiment of the invention.
Figure 9D:
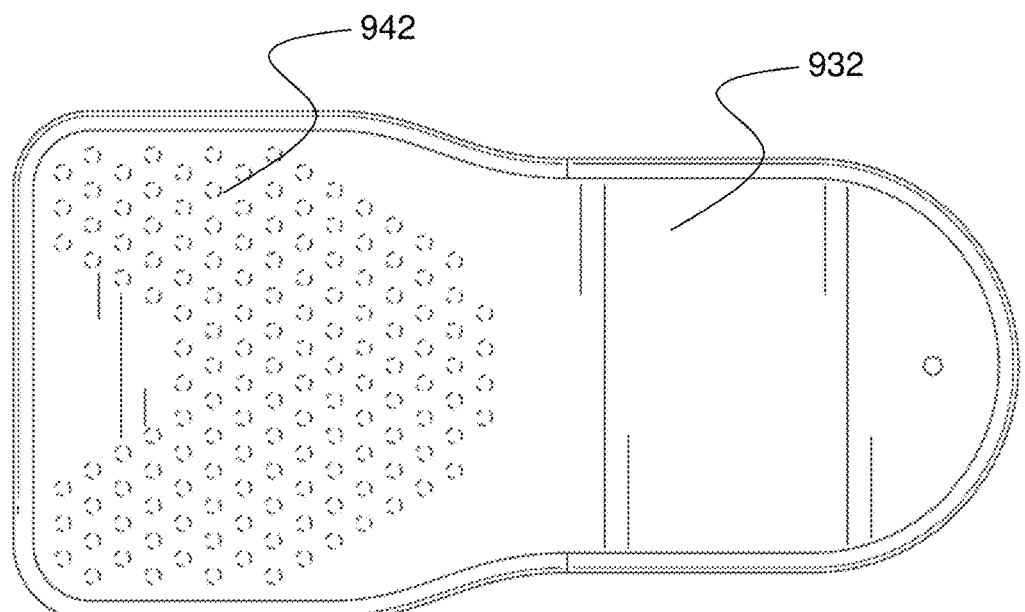
FIG. 9D is a diagram showing a bottom view of a mouthpiece in accordance with an illustrative embodiment of the invention.
Figure 10A:
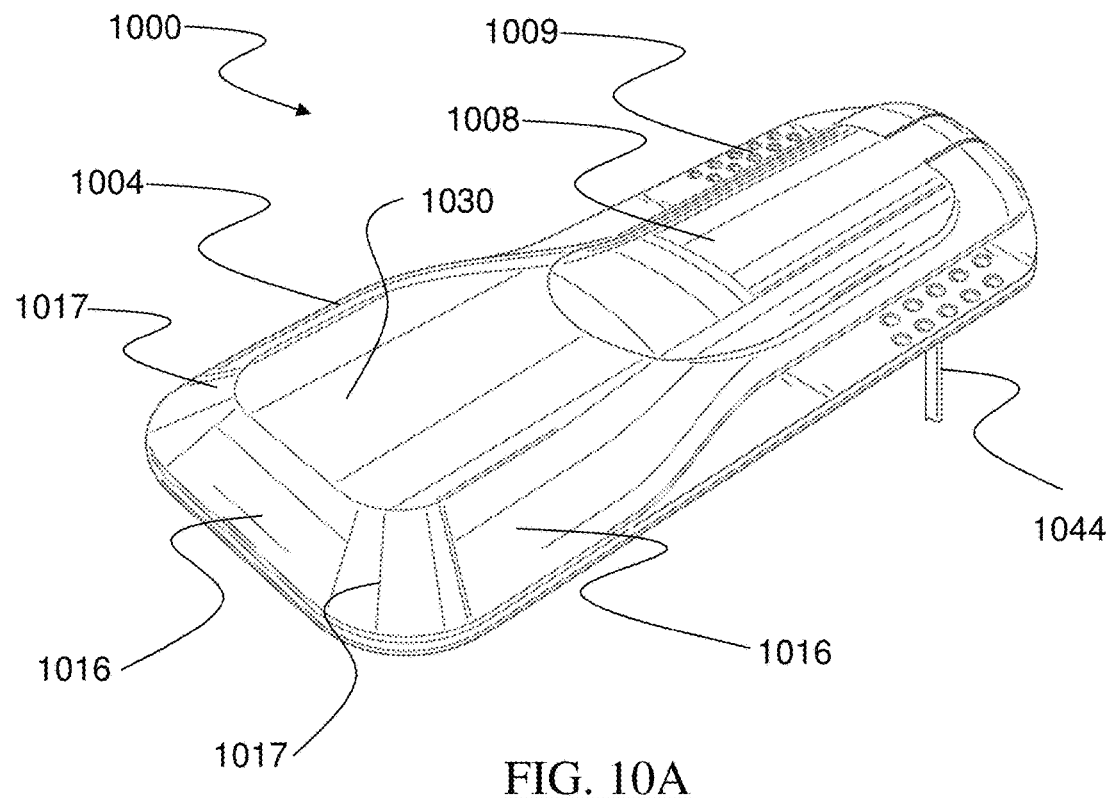
FIG. 10A is a diagram showing an isometric view of a mouthpiece in accordance with an illustrative embodiment of the invention.
Figure 10B:
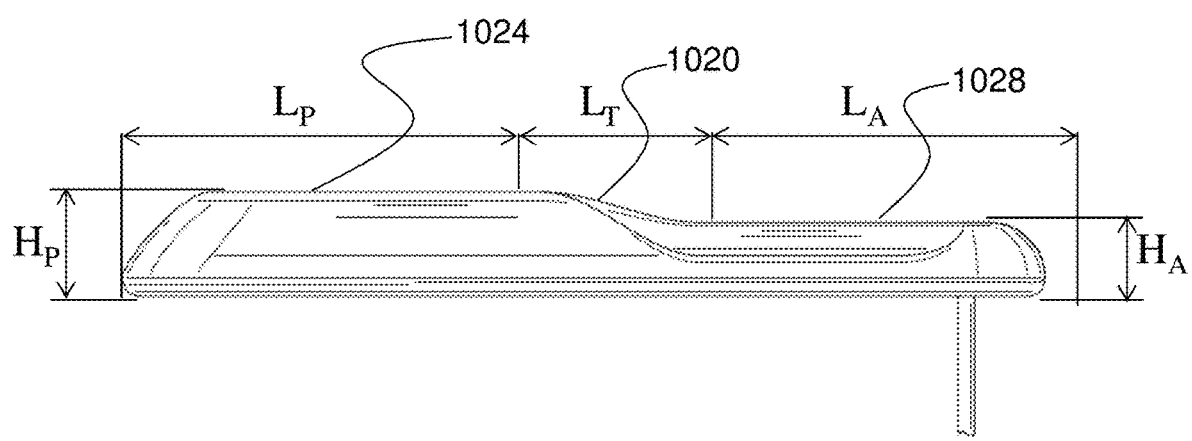
FIG. 10B is a diagram showing a side view of a mouthpiece in accordance with an illustrative embodiment of the invention.
Figure 10C:
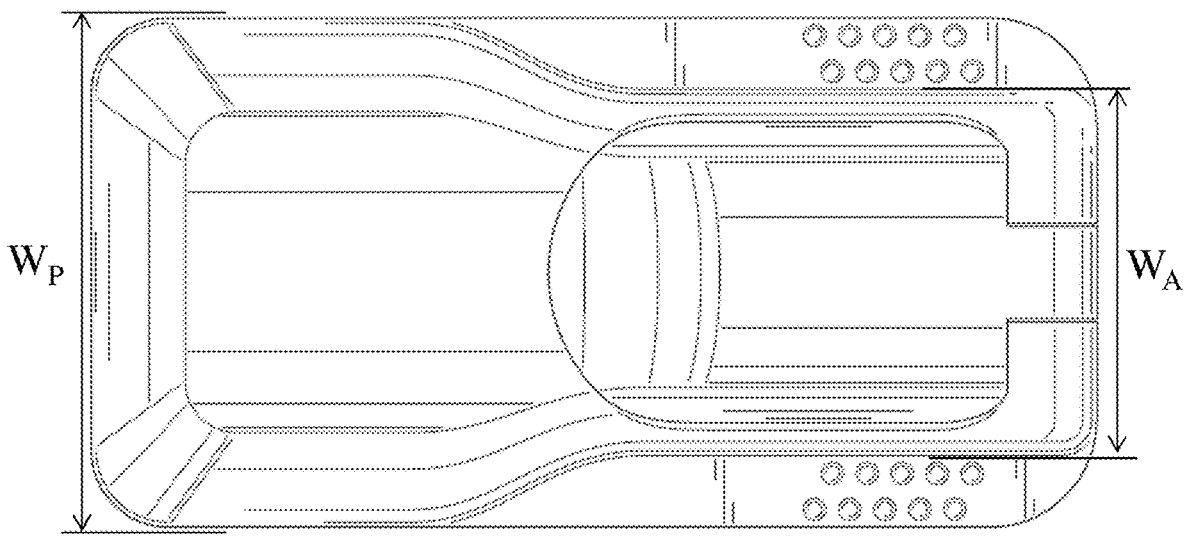
FIG. 10C is a diagram showing a top view of a mouthpiece in accordance with an illustrative embodiment of the invention.
Figure 10D:
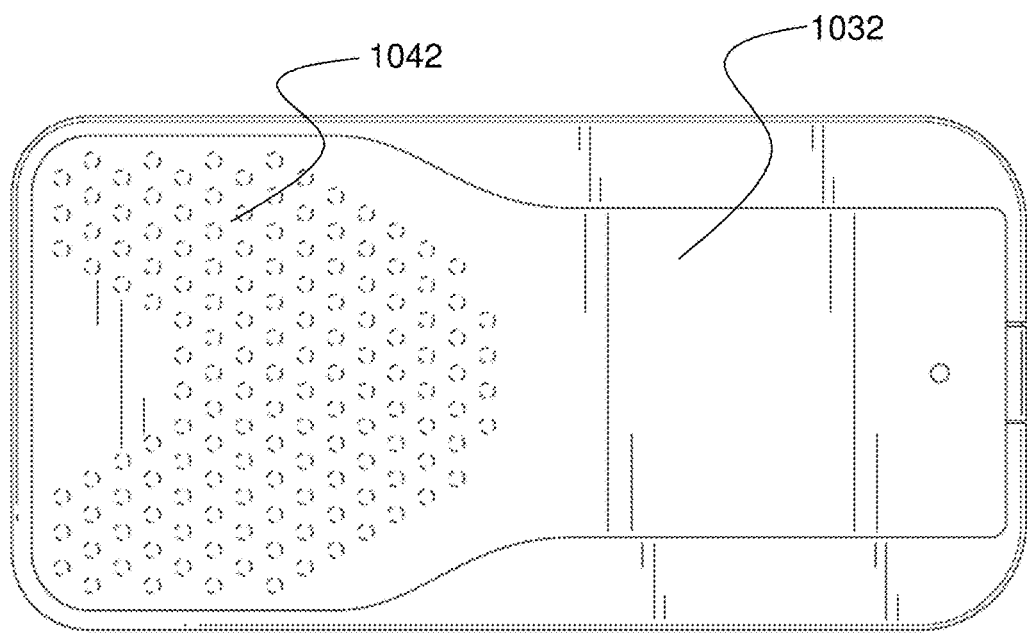
FIG. 10D is a diagram showing a bottom view of a mouthpiece in accordance with an illustrative embodiment of the invention.

FIGS. 2A and 2B show a non-invasive neurostimulation system 100. The non-invasive neurostimulation system 100 includes a controller 120 and a mouthpiece 140. The controller 120 includes a receptacle 126 and pushbuttons 122. The mouthpiece 140 includes an electrode array 142 and a cable 144. The cable 144 connects to the receptacle 126, providing an electrical connection between the mouthpiece 140 and the controller 120. In some embodiments, the controller 120 includes a cable. In some embodiments, the mouthpiece 140 and the controller 120 are connected wirelessly (e.g., without the use of a cable). During operation, a patient activates the neurostimulation system 100 by actuating one of the pushbuttons 122. In some embodiments, the neurostimulation system 100 periodically transmits electrical pulses to determine if the electrode array 142 is in contact with the patient's tongue and automatically activates based on the determination. After activation, the patient can start an NINM treatment session, stop the NINM treatment session, or pause the NINM treatment session by pressing one of the pushbuttons 122. In some embodiments, the neurostimulation system 100 periodically transmits electrical pulses to determine if the electrode array 142 is in contact with the patient's tongue and automatically pauses the NINM treatment session based on the determination. During an NINM treatment session, the patient engages in an exercise or other activity designed to facilitate neurorehabilitation. For example, during an NINM treatment session, the patient can engage in a physical exercise, a mental exercise, or a cognitive exercise. In some embodiments, the controller 120 has pushbuttons on both arms. In some embodiments, a mobile device can be used in conjunction with the controller 120 and the mouthpiece 140. The mobile device can include a software application that allows a user to activate the neurostimulation system 100 and start or stop an NINM treatment session by for example, pressing a button on the mobile device, or speaking a command into the mobile device. The mobile device can obtain patient information and treatment session information before, during, or after an NINM treatment session. In some embodiments, the controller 120 includes a secure cryptoprocessor that holds a secret key, to be described in more detail below in connection with FIGS. 9A and 9B. The secure cryptoprocessor is in communication with a microcontroller. The secure cryptoprocessor can be tamper proof. For example, if outer portions of the cryptoprocessor are removed in an attempt to access the secret key, the cryptoprocessor erases all memory, preventing unauthorized access of the secret key.

Figure 2C:
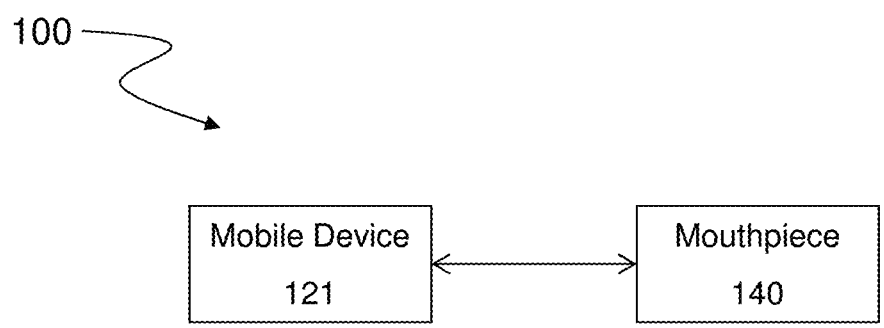
FIG. 2C is a diagram showing a neurostimulation system according to an illustrative embodiment of the invention.

FIG. 2C shows a non-invasive neurostimulation system 100. As shown, a mobile device 121 is in communication with a mouthpiece 140. More specifically, the mobile device 121 includes a processor running a software application that facilitates communications with the mouthpiece 140. The mobile device 121 can be, for example, a mobile phone, a portable digital assistant (PDA), or a laptop. The mobile device 121 can communicate with the mouthpiece 140 by a wireless or wired connection. During operation, a patient activates the neurostimulation system 100 via the mobile device 121. After activation, the patient can start an NINM treatment session, stop the NINM treatment session, or pause the NINM treatment session by manipulating the mobile device 121. During an NINM treatment session, the patient engages in an exercise or activity designed to provide neurorehabilitation. For example, during an NINM treatment session, the patient can engage in a physical exercise, a mental exercise, or a cognitive exercise.

Figure 3A:
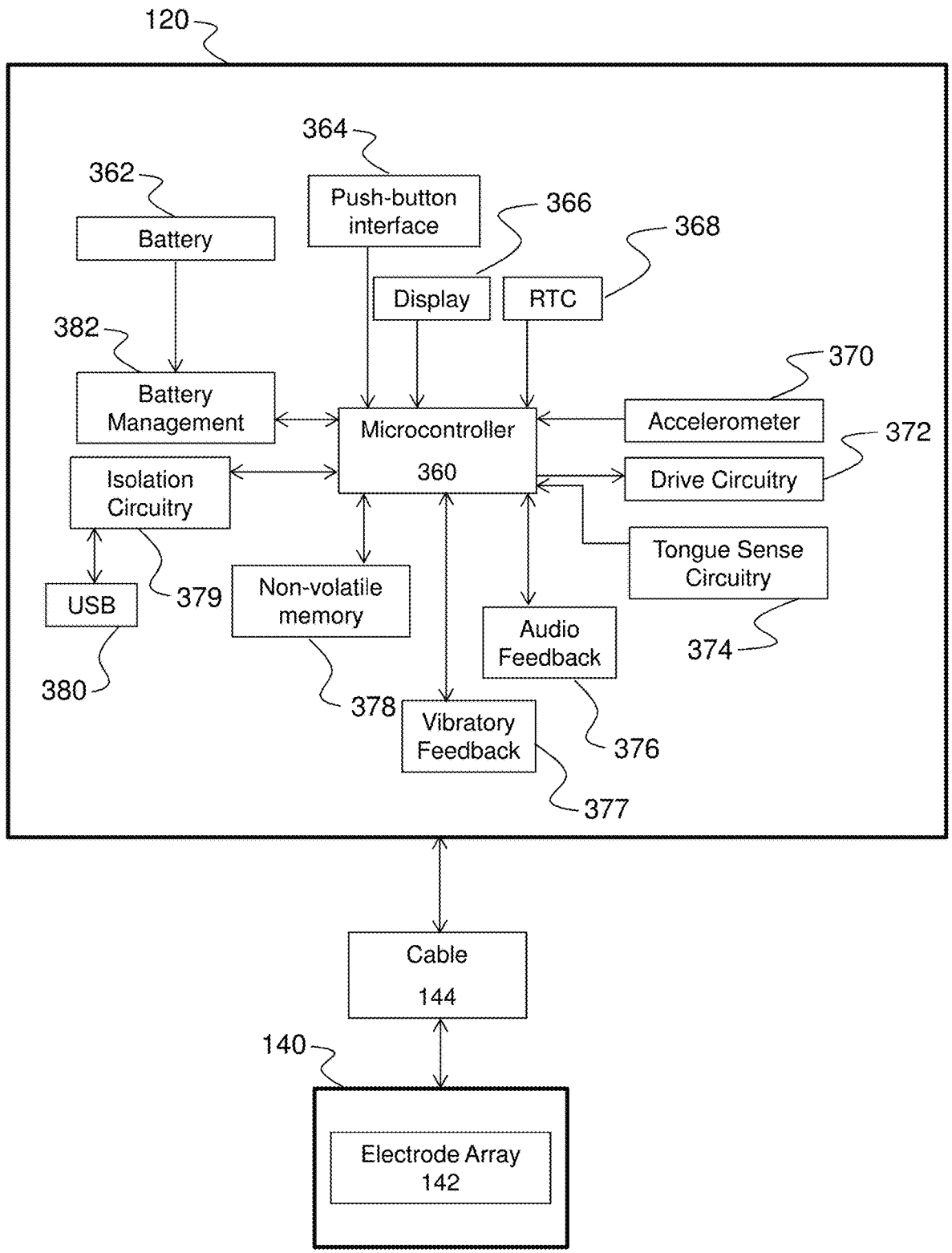
FIG. 3A is a diagram showing a more detailed view of the neurostimulation system depicted in FIGS. 2A and 2B.

FIG. 3A shows the internal circuitry housed within the controller 120. The circuitry includes a microcontroller 360, isolation circuitry 379, a universal serial bus (USB) connection 380, a battery management controller 382, a battery 362, a push-button interface 364, a display 366, a real time clock 368, an accelerometer 370, drive circuitry 372, tongue sense circuitry 374, audio feedback circuitry 376, vibratory feedback circuitry 377, and a non-volatile memory 378. The drive circuitry 372 includes a multiplexor, and an array of resistors to control voltages delivered to the electrode array 142. The microcontroller 360 is in electrical communication with each of the components shown in FIG. 3A. The isolation circuitry 379 provides electrical isolation between the USB connection 380 and all other components included in the controller 120. Additionally, the circuitry shown in FIG. 3A is in communication with the mouthpiece 140 via the external cable 144. During operation, the microcontroller 360 receives electrical power from battery 362 and can store and retrieve information from the non-volatile memory 378. The battery can be charged via the USB connection 380. The battery management circuitry controls the charging of the battery 362. A patient can interact with the controller 120 via the push-button interface 122 that converts the patient's pressing of a button (e.g. an info button, a power button, an intensity-up button, an intensity-down button, and a start/stop button) into an electrical signal that is transmitted to the microcontroller 360. For example, a therapy session can be started when the patient presses a start/stop button after powering on the controller 120. During the therapy session, the drive circuitry 372 provides an electrical signal to the mouthpiece 140 via the cable 144. The electrical signal is communicated to the patient's intraoral cavity via the electrode array 142. The accelerometer 370 can be used to provide information about the patient's motion during the therapy session. Information provided by the accelerometer 370 can be stored in the non-volatile memory 378 at a coarse or detailed level. For example, a therapy session aggregate motion index can be stored based on the number of instances where acceleration rises above a predefined threshold, with or without low pass filtering. Alternatively, acceleration readings could be stored at a predefined sampling interval. The information provided by the accelerometer 370 can be used to determine if the patient is engaged in a physical activity. Based on the information received from the accelerometer 370, the microcontroller 360 can determine an activity level of the patient during a therapy session. For example, if the patient engages in a physical activity for 30 minutes during a therapy session, the accelerometer 370 can periodically communicate (e.g. once every second) to the microcontroller 360 that the sensed motion is larger than a predetermined threshold (e.g. greater than 1 m/s$^2$). In some embodiments, the accelerometer data is stored in the non-volatile memory 378 during the therapy session and transmitted to the mobile device 121 after the therapy session has ended. After the therapy session has ended, the microcontroller 360 can record the amount of time during the therapy session in which the patient was active. In some embodiments, the recorded information can include other data about the therapy session (e.g., the date and time of the session start, the average intensity of electrical neurostimulation delivered to the patient during the session, the average activity level of the patient during the session, the total session time the mouthpiece has been in the patient's mouth, the total session pause time, the number of session shorting events, and/or the length of the session or the type of exercise or activity performed during the therapy session) and can be transmitted to a mobile device. A session shorting event can occur if the current transmitted from the drive circuitry to the electrode array 142 exceeds a predetermined threshold or if the charge transmitted from the drive circuitry to the electrode array exceeds a predetermined threshold over a predetermined time interval. After a session shorting event has occurred, the patient must manually press a pushbutton to resume the therapy session. The real time clock (RTC) 368 provides time and date information to the microcontroller 360. In some embodiments, the controller 120 is authorized by a physician for a predetermined period of time (e.g., two weeks). The RTC 368 periodically communicates date and time information to the microcontroller 360. In some embodiments, the RTC 368 is integrated with the microcontroller. In some embodiments, the RTC 368 is powered by the battery 362, and upon failure of the battery 362, the RTC 368 is powered by a backup battery. After the predetermined period of time has elapsed, the controller 120 can no longer initiate the delivery of electrical signals to the mouthpiece 140 and the patient must visit the physician to reauthorize use of the controller 120. The display 366 displays information received by the microcontroller 360 to the patient. For example, the display 366 can display the time of day, therapy information, battery information, time remaining in a therapy session, error information, and the status of the controller 120. The audio feedback circuitry 376 and vibratory feedback circuitry 377 can give feedback to a user when the device changes state. For example, when a therapy session begins, the audio feedback circuitry 376 and the vibratory feedback circuitry 377 can provide auditory and/or vibratory cues to the patient, notifying the patient that the therapy session has been initiated. Other possible state changes that may trigger audio and/or vibratory cues include pausing a therapy session, resuming a therapy session, the end of a timed session, canceling a timed session, or error messaging. In some embodiments, a clinician can turn off one or more of the auditory or vibratory cues to tailor the feedback to an individual patient's needs. The tongue sense circuitry 374 measures the current passing from the drive circuitry to the electrode array 142. Upon sensing a current above a predetermined threshold, the tongue sense circuitry 374 presents a high digital signal to the microcontroller 360, indicating that the tongue is in contact with the electrode array 142. If the current is below the predetermined threshold, the tongue sense circuitry 374 presents a low digital signal to the microcontroller 360, indicating that the tongue is not in contact or is in partial contact with the electrode array 142. The indications received from the tongue sense circuitry 374 can be stored in the non-volatile memory 378. In some embodiments, the display 366 can be an organic light emitting diode (OLED) display. In some embodiments, the display 366 can be a liquid crystal display (LCD). In some embodiments, a display 366 is not included with the controller 120. In some embodiments, neither the controller 120 nor the mouthpiece 140 includes a cable, and the controller 120 communicates wirelessly with the mouthpiece 140. In some embodiments, neither the controller 120 nor the mouthpiece 140 includes an accelerometer. In some embodiments, the drive circuitry 372 is located within the mouthpiece. In some embodiments, a portion of the drive circuitry 372 is located within the mouthpiece 140 and a portion of the drive circuitry 372 is located within the controller 120. In some embodiments, neither the controller 120 nor the mouthpiece 140 includes tongue sense circuitry 374. In some embodiments, the mouthpiece 140 includes a microcontroller and a multiplexer.

Figure 3B:
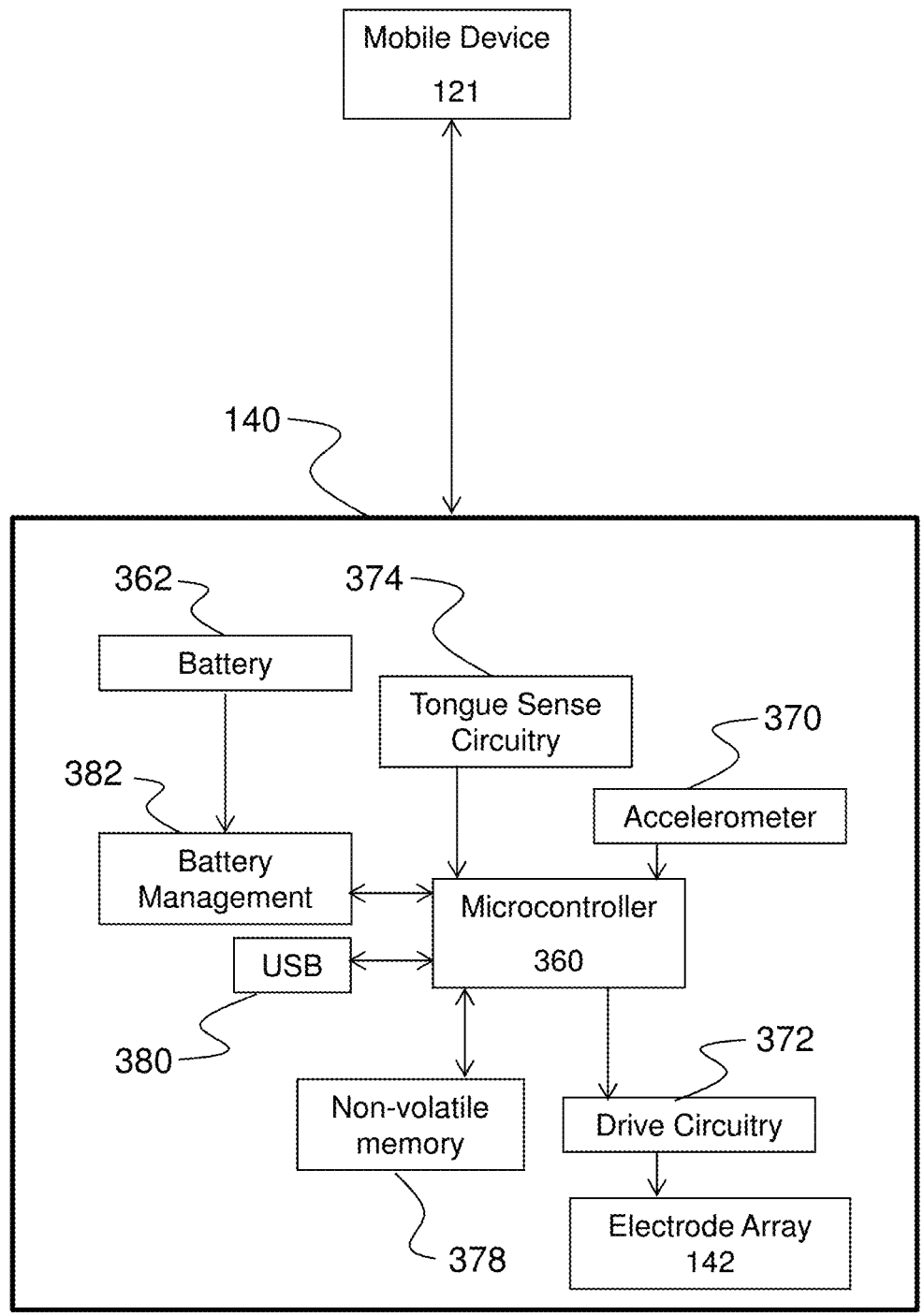
FIG. 3B is a diagram showing a more detailed view of the neurostimulation system depicted in FIG. 2C.

FIG. 3B shows a more detailed view of FIG. 2C. The mouthpiece 140 includes a battery 362, tongue sense circuitry 374, an accelerometer 370, a microcontroller 360, drive circuitry 372, a non-volatile memory 378, a universal serial bus controller (USB) 380, and battery management circuitry 382. During operation, the microcontroller receives electrical power from battery 362 and can store and retrieve information from the non-volatile memory 378. The battery can be charged via the USB connection 380. The battery management circuitry 382 controls the charging of the battery 362. A patient can interact with the mouthpiece 140 via the mobile device 121. The mobile device 121 includes an application (e.g. software running on a processor) that allows the patient to control the mouthpiece 140. For example, the application can include an info button, a power button an intensity-up button, an intensity-down button, and a start/stop button that are presented to the user visually via the mobile device 121. When the patient presses a button presented by the application running on the mobile device 121, a signal is transmitted to the microcontroller 360 housed within the mouthpiece 140. For example, a therapy session can be started when the patient presses a start/stop button on the mobile device 121. During the therapy session, the drive circuitry 372 provides an electrical signal to an electrode array 142 located on the mouthpiece 140. The accelerometer 370 can be used to provide information about the patient's motion during the therapy session. The information provided by the accelerometer 370 can be used to determine if the patient is engaged in a physical activity. Based on the information received from the accelerometer 370, the microcontroller 360 can determine an activity level of the patient during a therapy session. For example, if the patient engages in a physical activity for 30 minutes during a therapy session, the accelerometer 370 can periodically communicate (e.g. once every second) to the microcontroller 360 that the sensed motion is larger than a predetermined threshold (e.g. greater than 1 m/s$^2$). After the therapy session has ended, the microcontroller 360 can record the amount of time during the therapy session in which the patient was active. In some embodiments, the accelerometer 370 is located within the mobile device 121 and the mobile device 121 determines an activity level of a patient during the therapy session based on information received from the accelerometer 370. The mobile device can then record the amount of time during the therapy session in which the patient was active. The mobile device 121 includes a real time clock (RTC) 368 that provides time and date information to the microcontroller 360. In some embodiments, the mouthpiece 140 is authorized by a physician for a predetermined period of time (e.g., two weeks). After the predetermined period of time has elapsed, the mouthpiece 140 can no longer deliver electrical signals to the patient via the electrode array 142 and the patient must visit the physician to reauthorize use of the mouthpiece 140. In some embodiments, the mouthpiece 140 includes pushbuttons (e.g., an on/off button) and a patient can manually operate the mouthpiece 140 via the pushbuttons. After a therapy session, the mouthpiece 140 can transmit information about the therapy session to a mobile device. In some embodiments, the mouthpiece 140 does not include a USB controller 380 and instead communicates only via wireless communications with the controller.

Figure 3C:
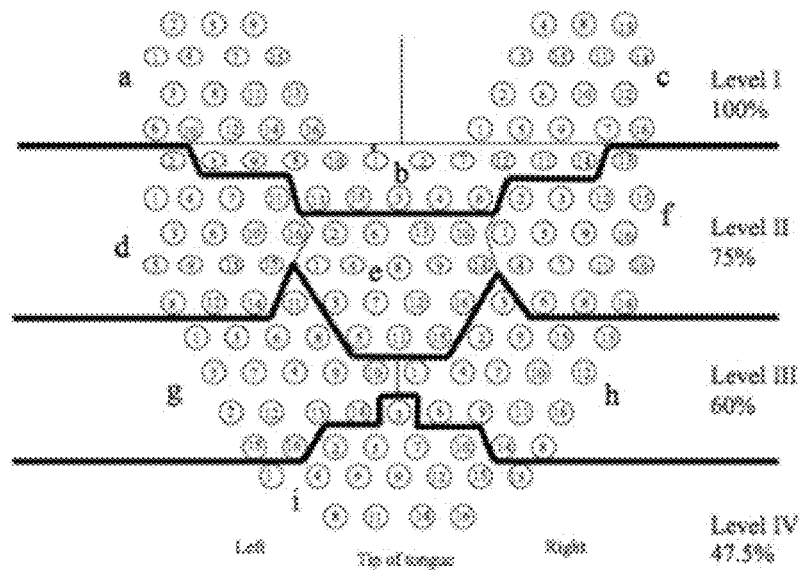
FIG. 3C is a diagram showing a more detailed view of an electrode array.

FIG. 3C shows a more detailed view of the electrode array 142. The electrode array 142 can be separated into 9 groups of electrodes, labelled a-i, with each group having 16 electrodes, except group b which has 15 electrodes. Each electrode within the group corresponds to one of 16 electrical channels. During operation, the drive circuitry can deliver a sequence of electrical pulses to the electrode array 142 to provide neurostimulation of at least one of the patient's trigeminal or facial nerve. The electrical pulse amplitude delivered to each group of electrodes can be larger near a posterior portion of the tongue and smaller at an anterior portion of the tongue. For example, the pulse amplitude of electrical signals delivered to groups a-c can be 19 volts or 100% of a maximum value, the pulse amplitude of electrical signals delivered to groups d-f can be 14.25 volts or 75% of the maximum value, the pulse amplitude of electrical signals delivered to groups g-h can be 11.4 volts or 60% of the maximum value, and the pulse amplitude of electrical signals delivered to group i can be 9.025 volts or 47.5% of the maximum value. In some embodiments, the maximum voltage is in the range of 0 to 40 volts. The pulses delivered to the patient by the electrode array 142 can be random or repeating. The location of pulses can be varied across the electrode array 142 such that different electrodes are active at different times, and the duration and/or intensity of pulses may vary from electrode. For oral tissue stimulation, currents of 0.5-50 mA and voltages of 1-40 volts can be used. In some embodiments, transient currents can be larger than 50 mA. The stimulus waveform may have a variety of time-dependent forms, and for cutaneous electrical stimulation, pulse trains and bursts of pulses can be used. Where continuously supplied, pulses may be 1-500 microseconds long and repeat at rates from 1-1000 pulses/second. Where supplied in bursts, pulses may be grouped into bursts of 1-100 pulses/burst, with a burst rate of 1-100 bursts/second.

Figure 3D:
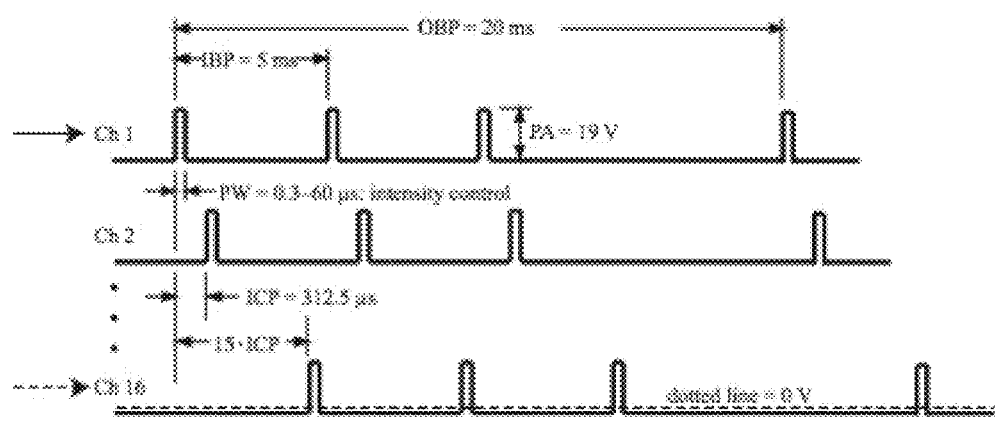
FIG. 3D is a graph showing an exemplary sequence of pulses for effecting neurostimulation of a patient.

In some embodiments, pulsed waveforms are delivered to the electrode array 142. FIG. 3D shows an exemplary sequence of pulses that can be delivered to the electrode array 142 by the drive circuitry 372. A burst of three pulses, each spaced apart by 5 ms is delivered to each of the 16 channels. The pulses in neighboring channels are offset from one another by 312.5 µs. The burst of pulses repeats every 20 ms. The width of each pulse can be varied from 0.3-60 µs to control an intensity of neurostimulation (e.g., a pulse having a width of 0.3 µs will cause a smaller amount of neurostimulation than a pulse having a width of 60 µs).

Figure 4A:
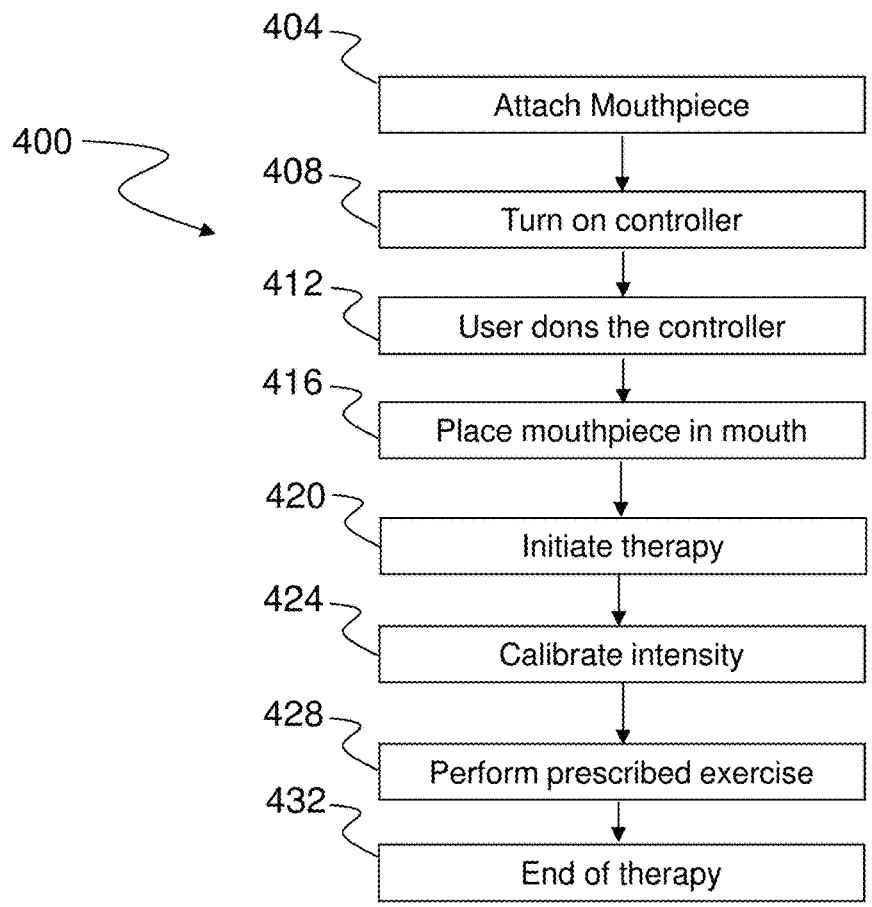
FIG. 4A is a flow chart illustrating a method in accordance with one embodiment for operating a neurostimulation system.

FIG. 4A shows a method of operation 400 of a controller 120 as described in FIGS. 2A, 2B and 3A. A patient attaches a mouthpiece 140 to a controller 120 (step 404). The patient turns on the controller 120 (step 408) using, for example, a power button. The patient places the controller 120 around his/her neck (step 412) as shown in FIG. 1B. The patient places a mouthpiece 140 in his/her mouth (step 416). The patient initiates a therapy session by pressing a start/stop button (step 420). During the therapy session, the controller 120 delivers electrical signals to the mouthpiece 140. The patient calibrates the intensity of the electrical signals (step 424). The patient raises the intensity of the electrical signals delivered to the mouthpiece by pressing an intensity-up button until the neurostimulation is above the patient's sensitivity level. The patient presses an intensity-down button until the neurostimulation is comfortable and non-painful. After the calibration step, the patient performs a prescribed exercise (step 428). The exercise can be cognitive, mental, or physical. In some embodiments, physical exercise includes the patient attempting to maintain a normal posture or gait, the patient moving his/her limbs, or the patient undergoing speech exercises. Cognitive exercises can include "brain training" exercises, typically computerized, that are designed to require the use of attention span, memory, or reading comprehension. Mental exercises can include visualization exercises, meditation, relaxation techniques, and progressive exposure to "triggers" for compulsive behaviors.

In some embodiments, the patient can rest for a period of time during the therapy session (e.g. the patient can rest for 2 minutes during a 30 minute therapy session). After a predetermined period of time (for example, thirty minutes) has elapsed, the therapy session ends (step 432) and the controller 120 stops delivering electrical signals to the mouthpiece 140. In some embodiments, the intensity of electrical signals increases from zero to the last use level selected by the patient over a time duration in the range of 1-5 seconds after the patient starts a therapy session by pressing the start/stop button. In some embodiments, the intensity of electrical signals is set to a fraction of the last use level selected by the patient (e.g. ¾ of the last level selected) after the patient starts a therapy session by pressing the start/stop button. In some embodiments, the intensity of electrical signals increases from zero to a fraction of the last use level selected by the patient (e.g. ¾ of the last level selected) over a time duration in the range of 1-5 seconds after the patient starts a therapy session by pressing the start/stop button. In some embodiments, the intensity of electrical signals increases instantaneously from zero to the last use level selected by the patient after the patient starts a therapy session by pressing the start/stop button.

In some embodiments, the mouthpiece 140 is connected to the controller 120 after the controller 120 is turned on. In some embodiments, the mouthpiece 140 is connected to the controller 120 after the controller 120 is donned by the patient. In some embodiments, the patient calibrates the intensity of the electrical signals before initiating a therapy session. In some embodiments, a patient performs an initial calibration of the intensity of electrical signals in the presence of a clinician and does not calibrate the intensity of the electrical signals during subsequent treatments performed in the absence of a clinician.

Figure 4B:
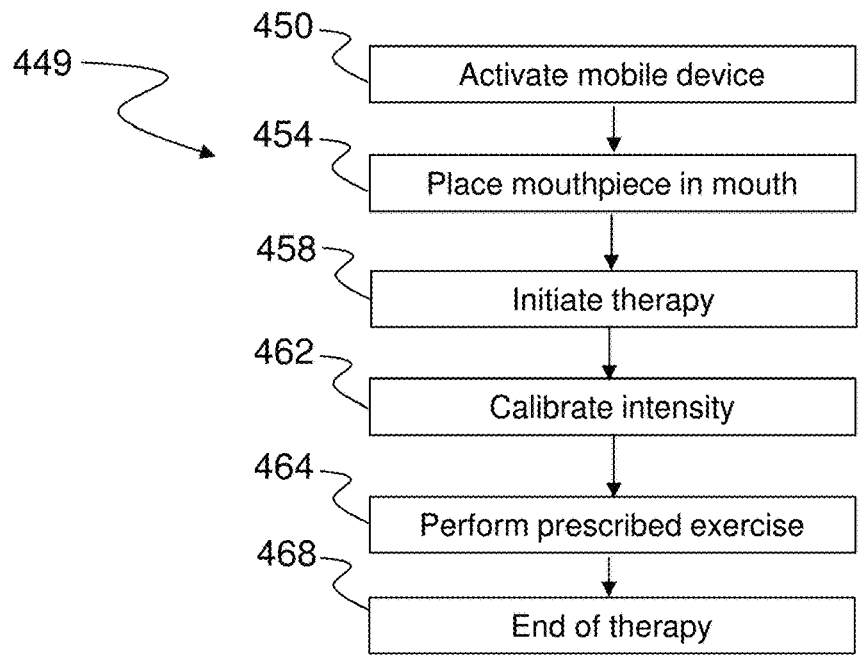
FIG. 4B is a flow chart illustrating a method in accordance with one embodiment for operating a neurostimulation system.
Figure 5A:
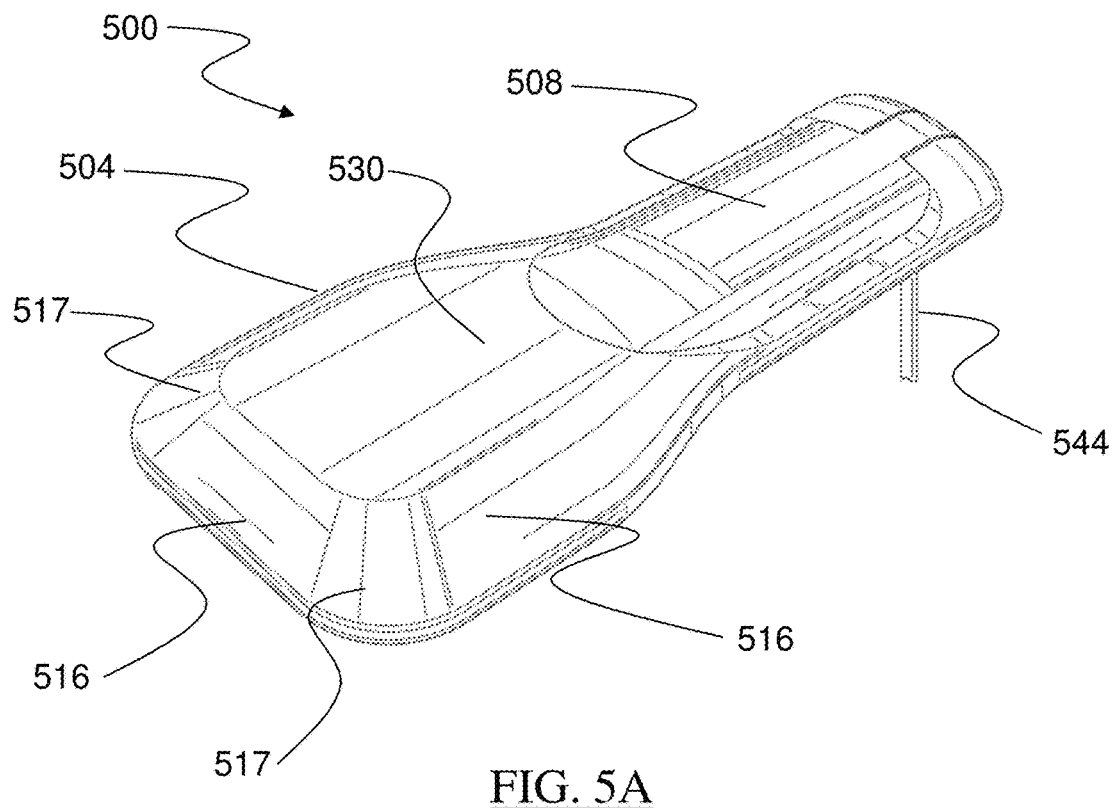
FIG. 5A is a diagram showing an isometric view of a mouthpiece in accordance with an illustrative embodiment of the invention.
Figure 5B:
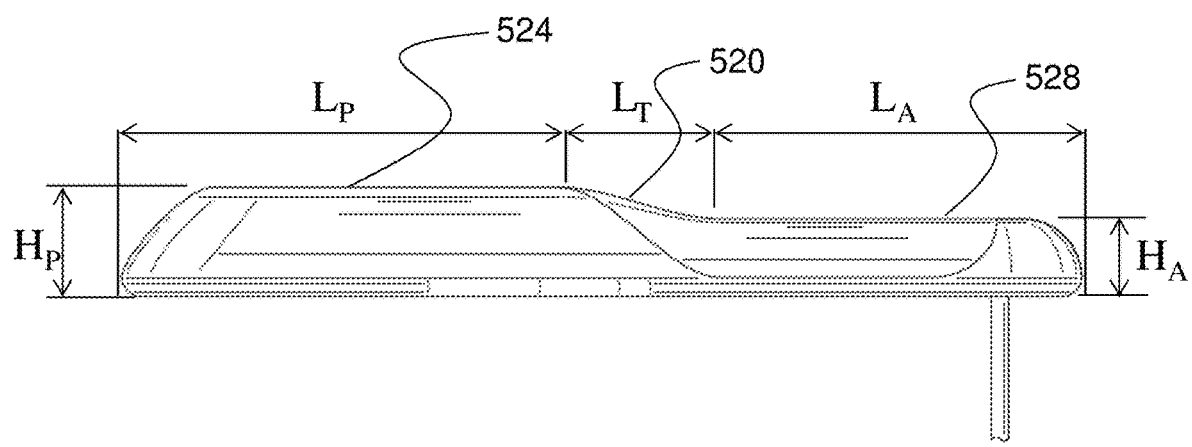
FIG. 5B is a diagram showing a side view of a mouthpiece in accordance with an illustrative embodiment of the invention.
Figure 5C:
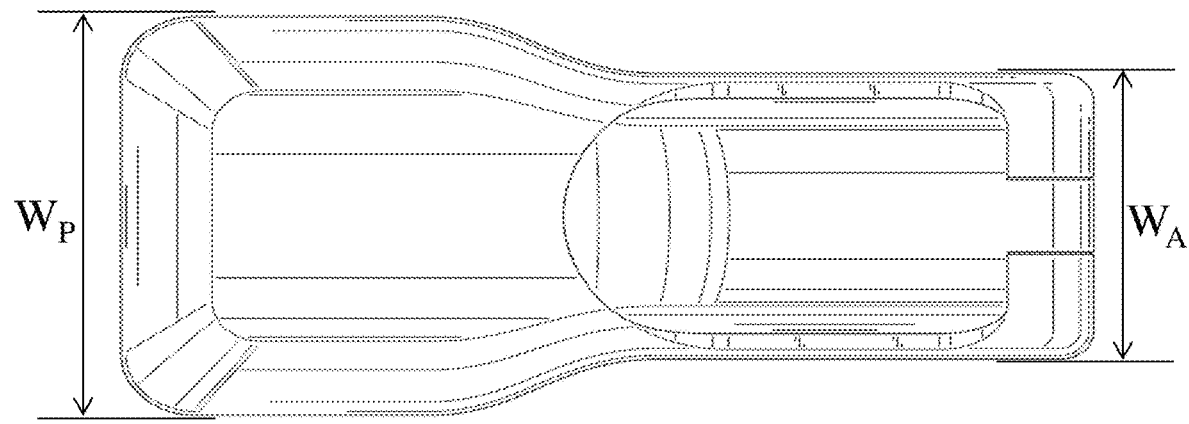
FIG. 5C is a diagram showing a top view of a mouthpiece in accordance with an illustrative embodiment of the invention.
Figure 5D:
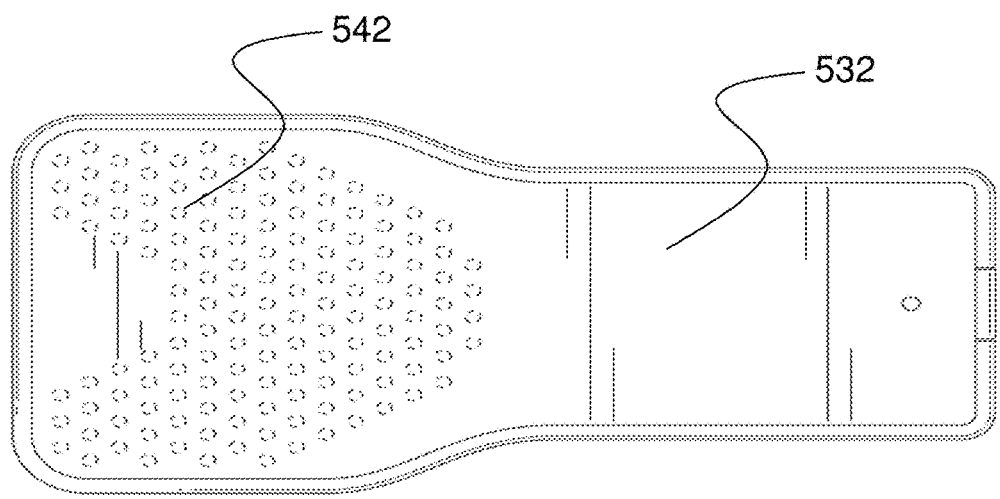
FIG. 5D is a diagram showing a bottom view of a mouthpiece in accordance with an illustrative embodiment of the invention.

FIG. 4B shows a method of operation 449 of the non-invasive neurostimulation system 100 described in FIGS. 2C and 3B. A patient activates a mobile device 121 (step 450). The patient places a mouthpiece 140 in his/her mouth (step 454). The patient initiates a therapy session by pressing a start/stop button within an application running on the mobile device 121 (step 458). During the therapy session, circuitry within the mouthpiece 140 delivers electrical signals to an electrode array 142 located on the mouthpiece 140. The patient calibrates the intensity of the electrical signals (step 462). The patient first raises the intensity of the electrical signals delivered to the mouthpiece 140 by pressing an intensity-up button located within an application running on the mobile device 121 until the neurostimulation is above the patient's sensitivity level. The patient presses an intensity-down button running within an application on the mobile device 121 until the neurostimulation is comfortable and non-painful. After the calibration step, the patient performs a prescribed exercise (step 464). The exercise can be cognitive, mental, or physical. In some embodiments, the patient can rest for a period of time during the therapy session (e.g. the patient can rest for 5 minutes during a 30 minute therapy session). After a predetermined period of time (for example, thirty minutes) has elapsed, the therapy session ends (step 468) and the circuitry located within the mouthpiece 140 stops delivering electrical signals to the electrode array 142. In some embodiments, the calibration of the intensity of the electrical signals takes place before the patient initiates a therapy session. FIGS. 5A-5D show a mouthpiece 500. The mouthpiece 500 includes a housing 504, a positioning pad 508, a transition region 520, a posterior region 524, an anterior region 528, a printed circuit board 532, internal circuitry, an electrode array 542, and a cable 544. The housing 504 includes chamfered or beveled surfaces 516, rounds 517, and a plateau 530. The mouthpiece 500 has three regions, a posterior region 524, a transition region 520, and an anterior region 528. The lengths of the posterior region, the transition region, and the anterior region are shown in FIG. 5B as $L_P$, $L_T$, and $L_A$ respectively. The maximum heights of the posterior region and the anterior region are shown in FIG. 5B as $H_P$ and $H_A$ respectively. The maximum widths of the posterior region and the anterior region are shown in FIG. 5C as $W_P$ and $W_A$ respectively. In some embodiments, $L_P$ is approximately 22.7 mm, $L_T$ is approximately 10.4 mm, $L_A$ is approximately 36.7 mm, $H_P$ is approximately 8.2 mm, $H_A$ is approximately 4.5 mm, $W_P$ is approximately 33.75 mm, and $W_A$ is approximately 27.4 mm. In some embodiments, $L_P$ is in the range of 17-30 mm, $L_T$ is in the range of 8 to 13 mm, $L_A$ is in the range of 27 to 45 mm, $H_P$ is in the range of 6 to 10 mm, $H_A$ is in the range of 3 to 5 mm, $W_P$ is in the range of 25 to 42 mm, and $W_A$ is in the range of 20 to 34 mm. The positioning pad 508 is attached to the housing 504 and can form a mesa in an anterior region 528 of the mouthpiece 500. The transition region 520 smoothly connects the anterior region 528 with the posterior region 524. The printed circuit board 532 attaches to the bottom side of the housing 504. In some embodiments, the printed circuit board 532 can be attached to the housing 504 by an adhesive. In some embodiments, the housing 504 is molded directly onto the printed circuit board 532. The internal circuitry is mounted to the top side of the printed circuit board 532 and is surrounded by the housing 504. The cable 544 is in communication with the internal circuitry and the internal circuitry is in communication with the electrode array 542.

During operation, a patient opens his/her mouth and places a portion of the mouthpiece 500 in his/her mouth to engage in an NINM therapy session. The patient relaxes his/her mouth to secure a position of the mouthpiece. In some embodiments, the patient bites down on the positioning pad 508 with his/her front teeth to secure a position of the mouthpiece. The patient's bottom teeth can contact the printed circuit board 532 and the patient's tongue contacts the electrode array 542. The internal circuitry delivers electrical neurostimulation signals to the patient's tongue via the electrode array 542. In some embodiments, the patient's molars contact a region of the printed circuit board 532 containing the electrode array 542.

The location of the center of gravity of the mouthpiece 500 determines if the mouthpiece 500 can rest in a patient's mouth when there is no biting force applied by the patient (e.g., when the patient's mouth is open or in a relaxed position). If the center of gravity is located in an anterior region of the mouthpiece, the mouthpiece tends to fall out of the patient's mouth in the absence of an applied biting force or external mounting apparatus. If the center of gravity is located in a posterior portion of the mouthpiece, the mouthpiece will tend to rest within the patient's mouth, even in the absence of an applied biting force. Adjusting the center of gravity of the mouthpiece 500 can be achieved by various approaches including adjusting the density and/or volume of the anterior and posterior regions of the mouthpiece. In some embodiments, the length and/or position of the transition region 520 can be adjusted to locate the center of gravity within the posterior region 524 of the mouthpiece. In some embodiments, the posterior region of the mouthpiece corresponds to the region of the mouthpiece that rests behind the patient's teeth during an NINM therapy session. In some embodiments, the center of gravity is located behind the patient's teeth during an NINM therapy session. In some embodiments, the patient's teeth act as a fulcrum and the center of gravity of the mouthpiece rests behind the patient's teeth to allow the mouthpiece to remain in the patient's mouth, even when the patient's mouth is in a relaxed state. In some embodiments, the patient's lips act as a fulcrum and the center of gravity of the mouthpiece rests behind the patient's lips to allow the mouthpiece to remain in the patient's mouth, even when the patient's mouth is in a relaxed state.

In some embodiments, the density throughout the mouthpiece 500 is approximately constant and a volume of the posterior region is adjusted to locate the center of gravity of the mouthpiece within the posterior region. For example, the posterior region of the mouthpiece can have an approximately equal average length, but a larger average height and/or average width than the anterior region of the mouthpiece, resulting in a center of gravity located within the posterior region. In another example, the posterior region of the mouthpiece can have an approximately equal average width, but a larger average height and/or average length than the anterior region of the mouthpiece, resulting in a center of gravity located within the posterior region. In yet another example, the posterior region of the mouthpiece can have an approximately equal average height, but a larger average width and/or average length than the anterior region of the mouthpiece, resulting in a center of gravity located within the posterior region. In some embodiments, a chamfer or bevel located on the housing 504 can be adjusted to change the volume of the posterior region (e.g., increasing the size of the bevel can in turn decrease the volume of the posterior region). In some embodiments, the location of the transition region can be adjusted to change the volume of the posterior region. For example, the location of the transition region 520 can determine the length of the posterior region and the anterior region. For example, by moving the transition region 520 towards the anterior region 528, the length and volume of the anterior region decrease while the length and volume of the posterior region increase, causing the center of gravity of the mouthpiece 500 to move towards the posterior region. In another example, by moving the transition region 520 towards the posterior region 524, the length and volume of the posterior region decrease while the length and volume of the anterior region increase, causing the center of gravity of the mouthpiece 500 to move towards the anterior region. In some embodiments, the mouthpiece can be constructed from one or more of the following materials: glass filled nylon, nylon, thermoplastic polyurethane (TPU), thermoplastic elastomer (TPE), silicone, acrylonitrile butadiene styrene (ABS), and polycarbonate.

In some embodiments, the average density of the posterior region is smaller than the average density of the anterior region. The volume of the posterior region can be adjusted to locate the center of gravity of the mouthpiece within the posterior region. For example, the center of gravity can be moved to the posterior region of the mouthpiece by increasing the volume of the posterior region (e.g. by increasing the length, height, or width of the posterior region) until the product of the density of the posterior region and the volume of the posterior region is greater than the product of the density of the anterior region and the volume of the anterior region.

In some embodiments, the average density of the posterior region or anterior region is adjusted to locate the center of gravity of the mouthpiece within the posterior region (e.g., a high density material such as polytetrafluoroethylene (PTFE), metal, or a metal alloy can be added and/or substituted into the posterior region to increase the average density of the posterior region). For example, the volume of the posterior region can be the same as the volume of the anterior region and the average density of the posterior region can be adjusted to be greater than the average density in the anterior region such that the center of gravity of the mouthpiece is located within the posterior region. In another example, the volume of the posterior region can be less than the volume of the anterior region and the average density of the posterior region can be adjusted to be greater than the average density in the anterior region such that the center of gravity of the mouthpiece is located within the posterior region. In yet another example, the volume of the posterior region can be greater than the volume of the anterior region and the average density of the posterior region can be adjusted to be greater than or equal to the average density in the anterior region such that the center of gravity of the mouthpiece is located within the posterior region. For example, the center of gravity can be moved to the posterior region of the mouthpiece by increasing the volume of the posterior region (e.g. by increasing the length, height, or width of the posterior region) until the volume of the posterior region is greater than the volume of the anterior region.

In some embodiments, the average density of the anterior region can be reduced to locate the center of gravity within the posterior region of the mouthpiece. For example, at least one portion of material can be removed from the interior of the anterior region of the mouthpiece, the removed portion being replaced by a material having a lower density than the removed portion (e.g., polyethylene, polypropylene, air, or vacuum), resulting in a decreased average density of the anterior region. The removal of material from the anterior region can be repeated until the product of the average density of the posterior region and the volume of the posterior region is greater than the product of the average density of the anterior region and the volume of the anterior region.

In some embodiments, a number of components can be added or removed from the printed circuit board 532 to adjust the center of gravity. For example, any number of resistors, capacitors, or integrated circuits can be removed from an anterior portion of the printed circuit board 532 such that the center of gravity of the mouthpiece is located within a posterior region 524 of the mouthpiece 500. In some embodiments, a second printed circuit board is added to the posterior region of the mouthpiece 500 such that the center of gravity of the mouthpiece is located within a posterior region 524 of the mouthpiece 500. The second printed circuit board can be located above the printed circuit board 532. In some embodiments, stainless steel or other metal weights are added to the printed circuit board 532 such that the center of gravity of the mouthpiece is located within a posterior region 524 of the mouthpiece 500.

In some embodiments, the weight of the cable 544 can be adjusted 500 such that the center of gravity of the mouthpiece is located within a posterior region 524 of the mouthpiece 500. For example, the weight of the cable 544 can be adjusted by selecting the density of the material forming the cable. In some embodiments, a cable strain relief mechanism can be adjusted such that the center of gravity of the mouthpiece is located within a posterior region 524 of the mouthpiece 500. For example, the total amount of material and density of material included in a strain relief mechanism can be selected to locate the center of gravity of the mouthpiece within a posterior region 524 of the mouthpiece 500.

In some embodiments, the shape of the mouthpiece provides forces that resist pulling of the mouthpiece 500 out of the patient's relaxed mouth. The width of the anterior region ($W_A$) and the height of the anterior region ($H_A$) are selected to allow the anterior region to pass through the patient's relaxed mouth without substantially contacting the patient's inner cheeks or lips. The width of the posterior region ($W_P$) and the height of the posterior region ($H_P$) are selected to cause the posterior region to make substantial contact with the patient's lips and/or inner cheeks. As the mouthpiece 500 is pulled out of the mouth, the inner cheeks and lips will be caused to open and/or deform, exerting forces on the mouthpiece that resist the pulling of the mouthpiece 500 out of the patient's mouth.

In some embodiments, the height of the posterior region 524 is selected such that the patient's teeth block the posterior region 524 from exiting the patient's mouth while the patient's mouth is in a relaxed state. The patient can open his/her jaw to unblock the posterior region 524 from exiting the patient's mouth. In some embodiments, the transition region, the chamfered or beveled surfaces 516, the rounds 517, and the plateau 530 are shaped to form a surface that substantially conforms to the roof of the patient's mouth, with a thin layer of saliva forming in between and facilitating a suction force that holds the mouthpiece 500 in the patient's mouth.

Figure 6A:
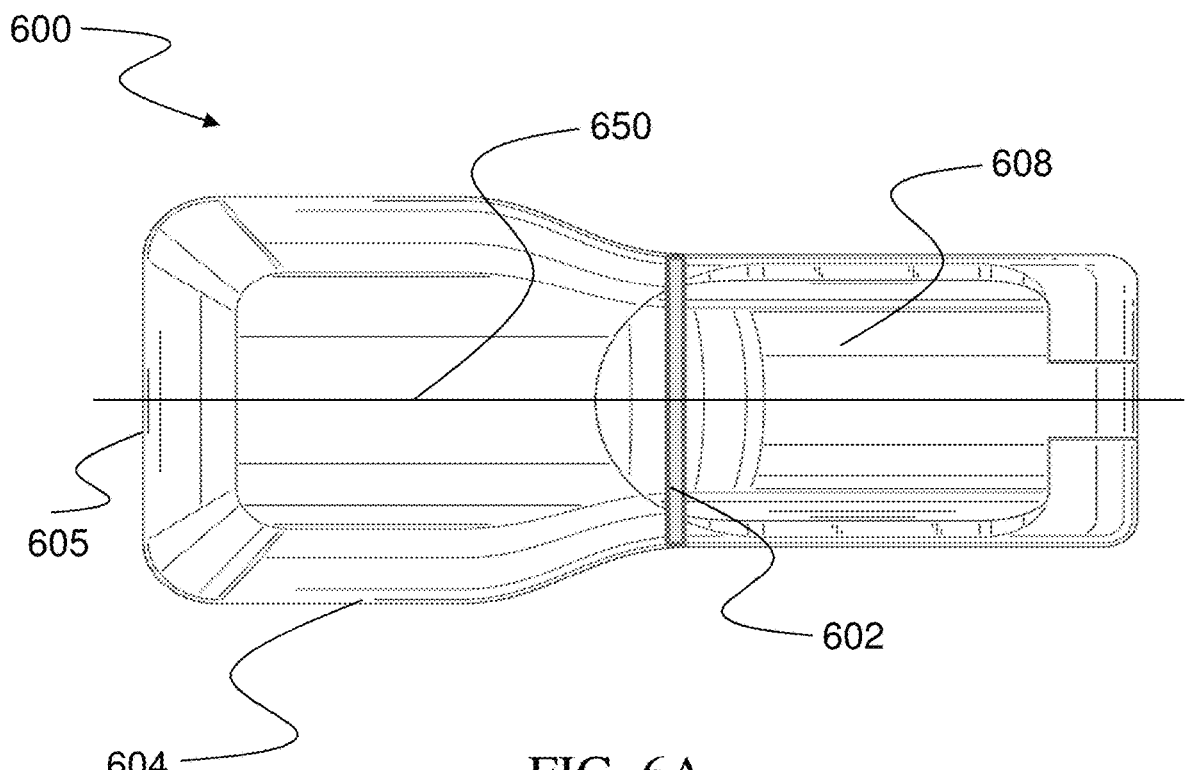
FIG. 6A is a diagram showing a top view of a mouthpiece in accordance with an illustrative embodiment of the invention.
Figure 6B:
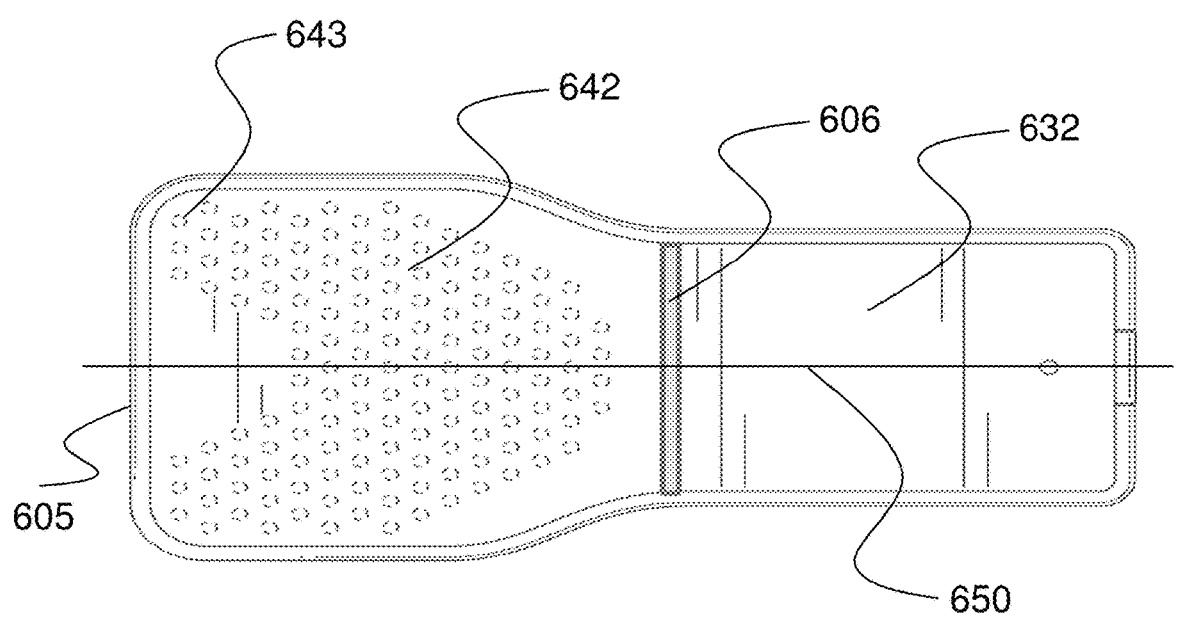
FIG. 6B is a diagram showing a bottom view of a mouthpiece in accordance with an illustrative embodiment of the invention.
Figure 6C:
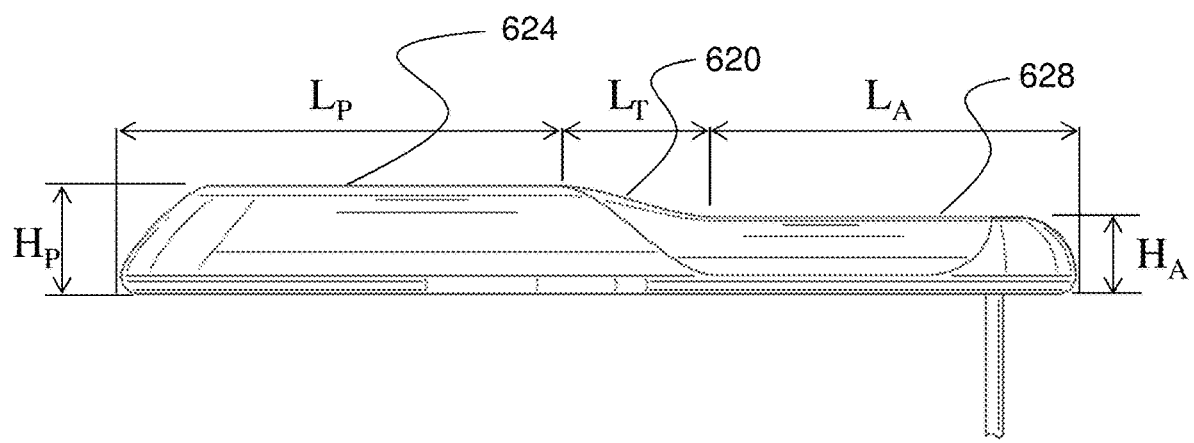
FIG. 6C is a diagram showing a side view of a mouthpiece in accordance with an illustrative embodiment of the invention.
Figure 7A:
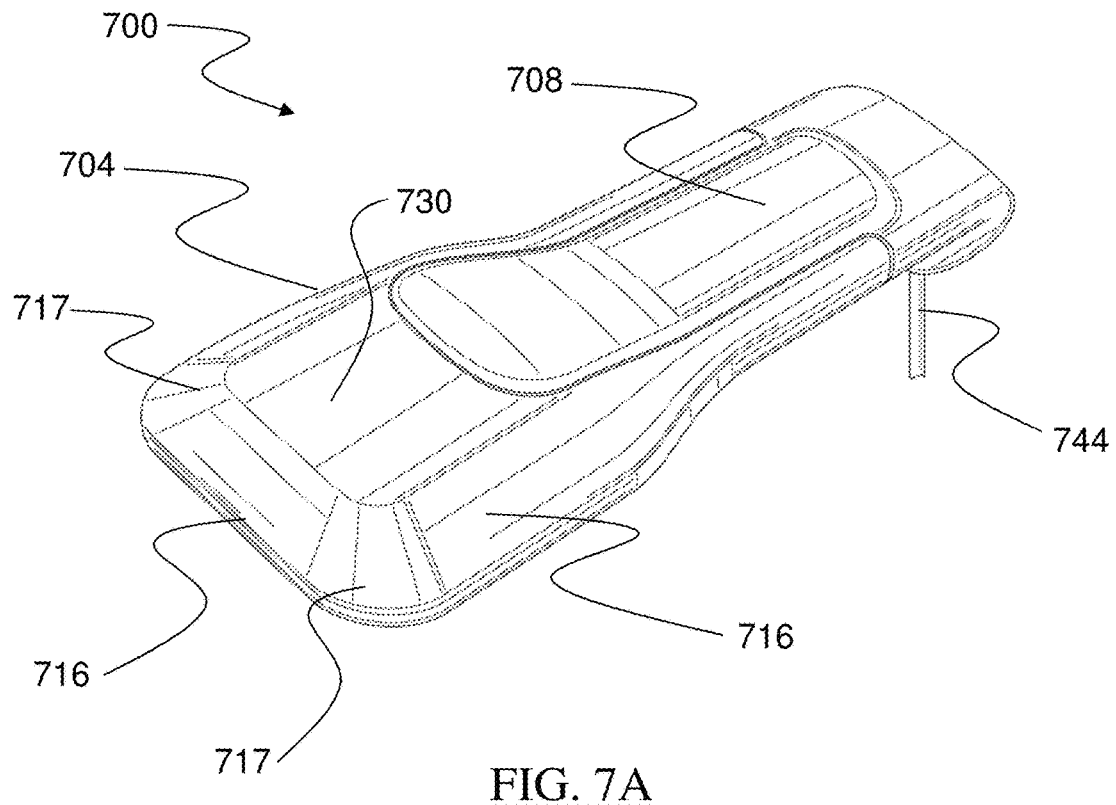
FIG. 7A is a diagram showing an isometric view of a mouthpiece in accordance with an illustrative embodiment of the invention.
Figure 7B:
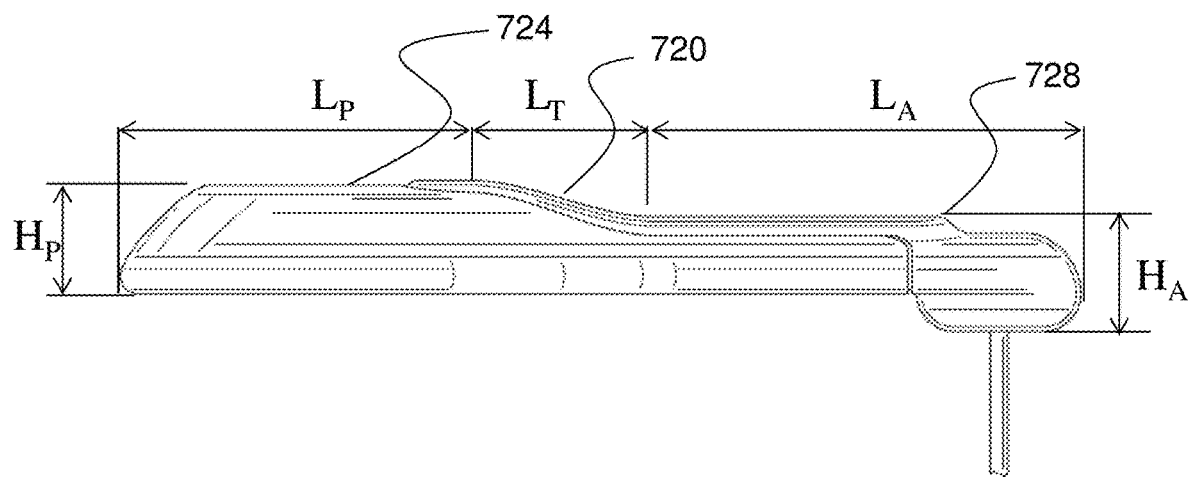
FIG. 7B is a diagram showing a side view of a mouthpiece in accordance with an illustrative embodiment of the invention.
Figure 7C:
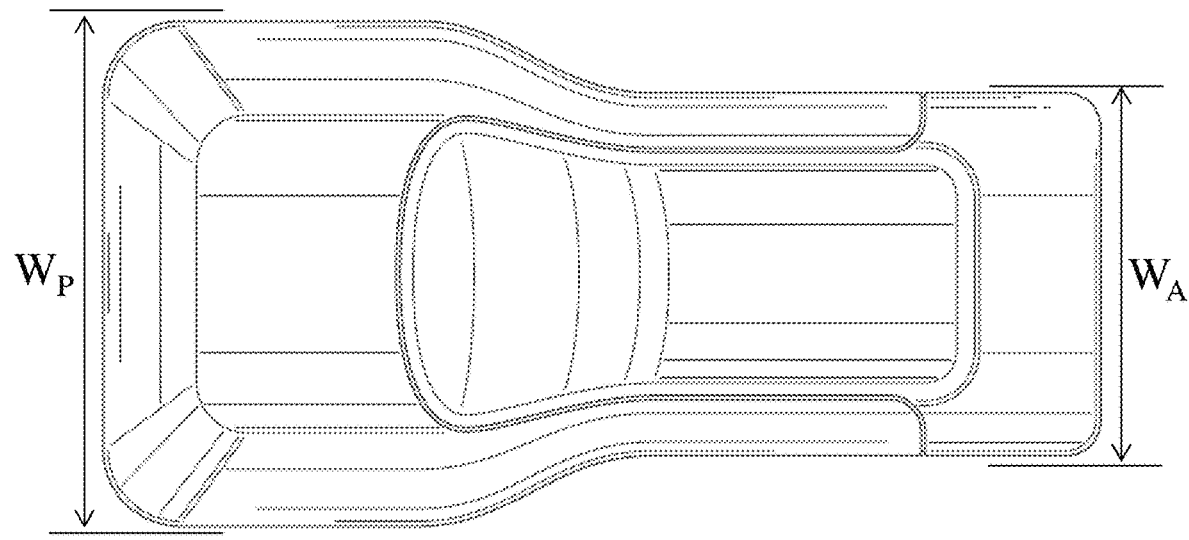
FIG. 7C is a diagram showing a top view of a mouthpiece in accordance with an illustrative embodiment of the invention.
Figure 7D:
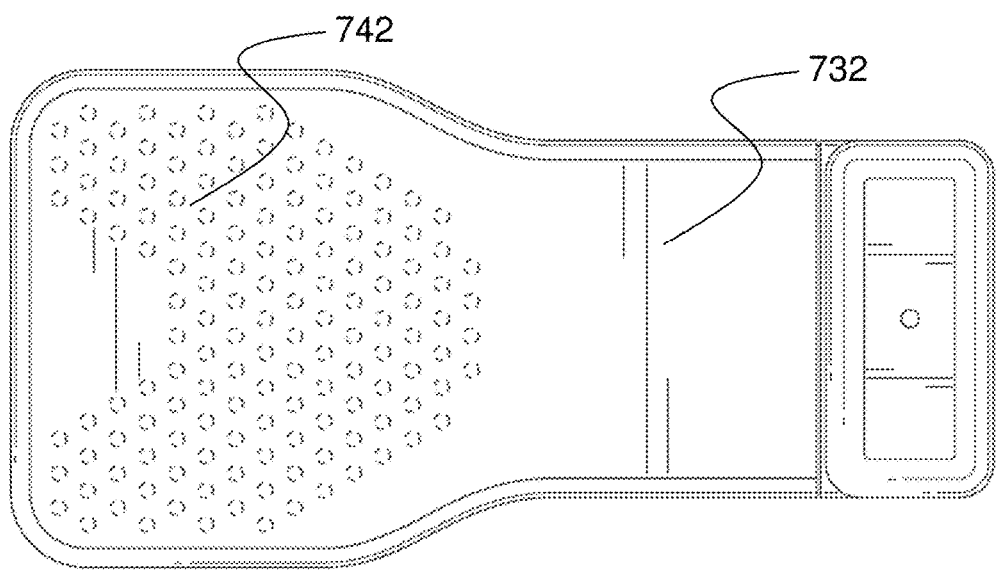
FIG. 7D is a diagram showing a bottom view of a mouthpiece in accordance with an illustrative embodiment of the invention.
Figure 8A:
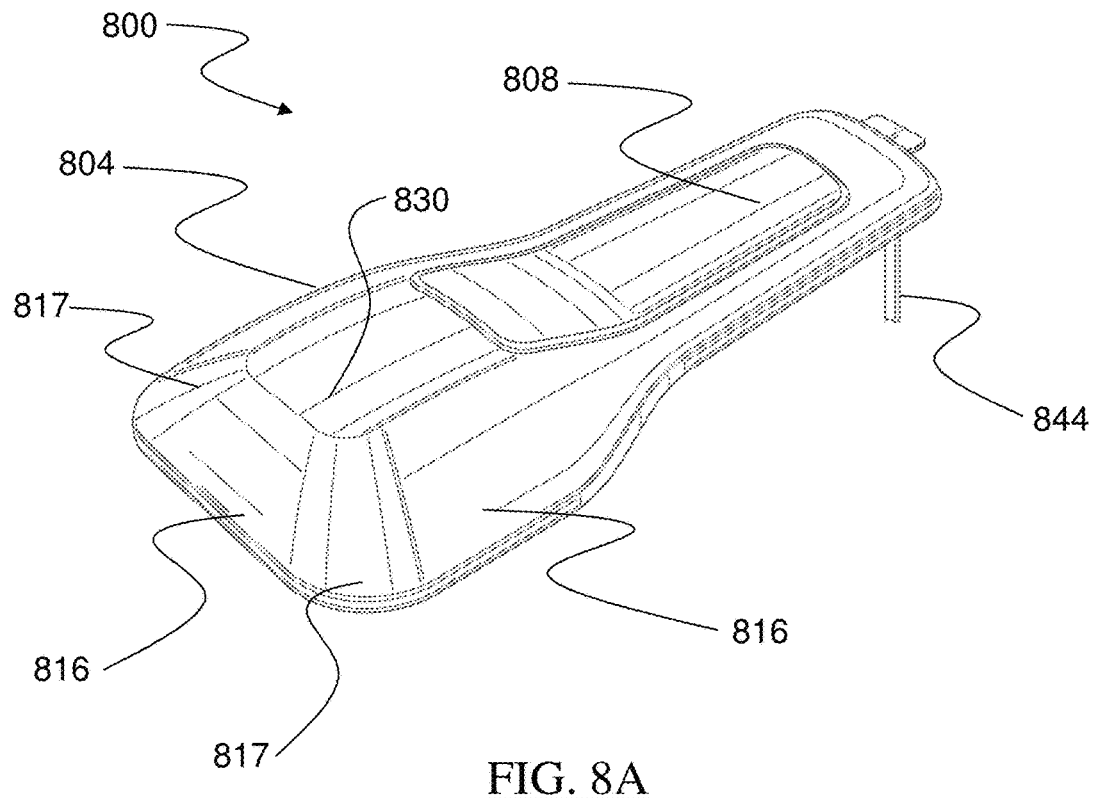
FIG. 8A is a diagram showing an isometric view of a mouthpiece in accordance with an illustrative embodiment of the invention.
Figure 8B:
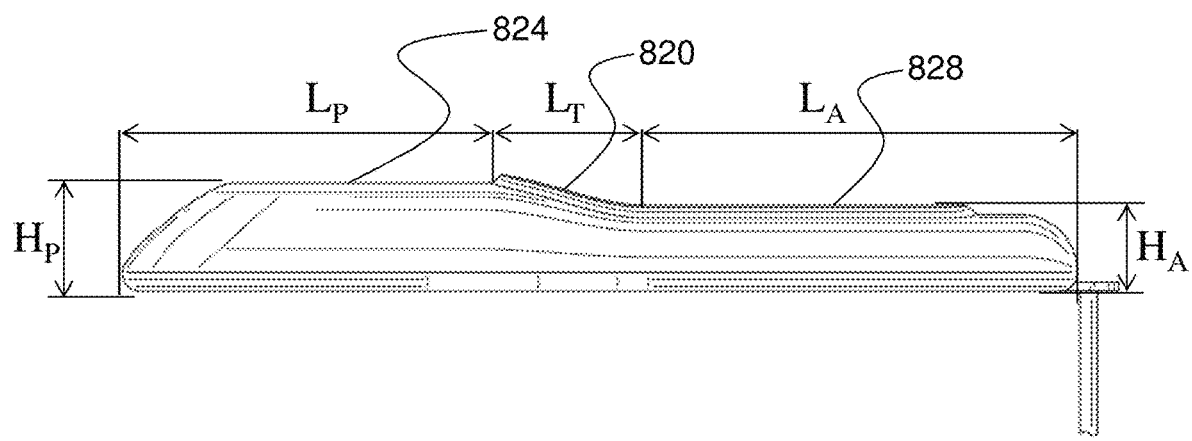
FIG. 8B is a diagram showing a side view of a mouthpiece in accordance with an illustrative embodiment of the invention.
Figure 8C:
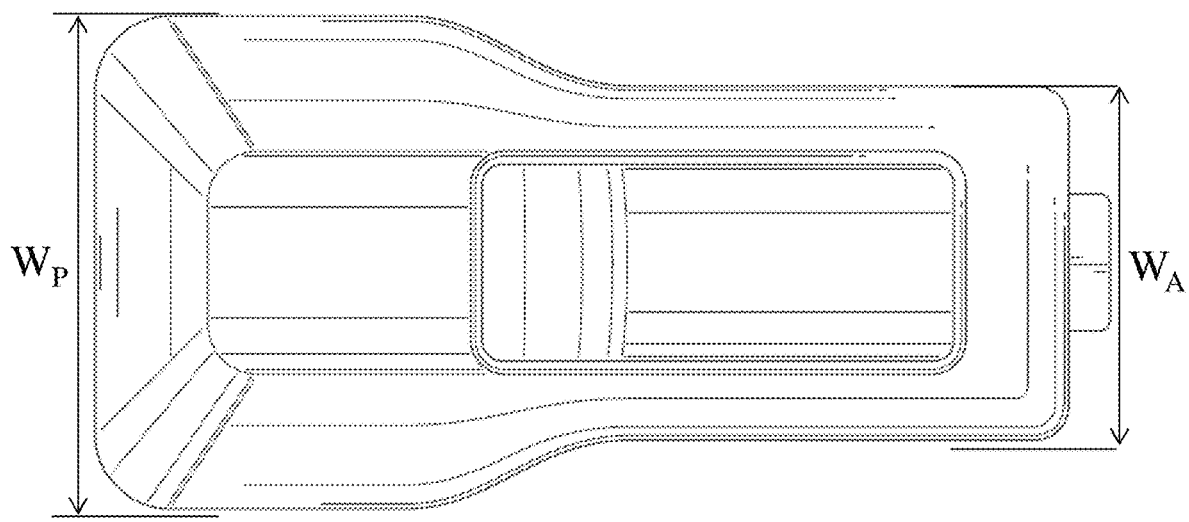
FIG. 8C is a diagram showing a top view of a mouthpiece in accordance with an illustrative embodiment of the invention.
Figure 8D:
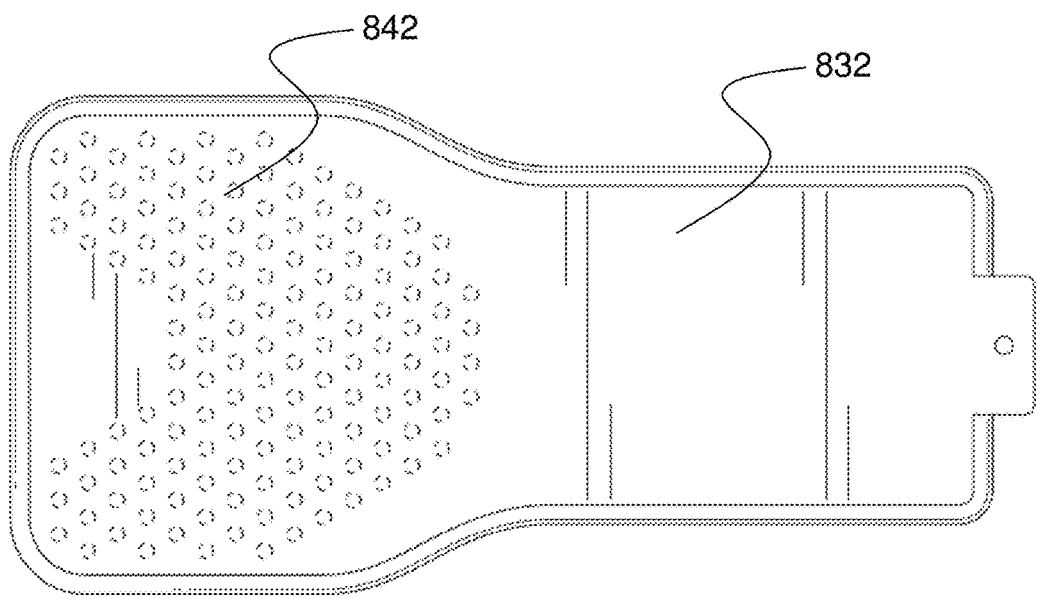
FIG. 8D is a diagram showing a bottom view of a mouthpiece in accordance with an illustrative embodiment of the invention.

FIGS. 6A-6C show a mouthpiece 600 having a longitudinal axis 650 and a posterior boundary 605. The mouthpiece 600 includes a housing 604, a positioning pad 608, a bottom locator 606, a top locator 602, a transition region 620, a posterior region 624, an anterior region 628, an electrode array 642, internal circuitry, and a printed circuit board 632. The electrode array 642 includes one or more posterior electrodes 643 that are nearest to the posterior boundary 605. The mouthpiece 600 is similar to the mouthpiece 500 with the exception of the two additional locators 602 and 606. During operation a patient inserts the mouthpiece 600 into his/her mouth and bites down on the mouthpiece. The internal circuitry delivers electrical neurostimulation signals to the patient's tongue via the electrode array 642 which contacts the patient's tongue.

The locators 602 and 606 can be used to position the mouthpiece 600 within the patient's mouth along the longitudinal axis 650. For example, the top locator 602 can include a trench traversing the width of the mouthpiece 600 that accommodates the patient's upper teeth. The patient can adjust the mouthpiece 600 until the patient's upper teeth contact the trench. Once the trench is in contact with the patient's upper teeth, the patient can bite down on the mouthpiece 600. The patient's upper teeth can remain in contact with the trench, securing the position of the mouthpiece along a longitudinal axis 650 of the mouthpiece 600. The trench can have a depth between 0.5 mm and 1 mm and a cross section shaped like an inverted step, a "U" or a "V". In some embodiments, the bottom locator 606 includes a trench that accommodates the patient's lower teeth. The position of the locators 602, 606 can be chosen to prevent the posterior region of the mouthpiece 600 from contacting any of the patient's anatomy that might cause gagging (e.g., the patient's tonsils, throat, or circumvallate papillae). Additionally, the position of the locators 602, 606 can be chosen to optimize the overlap between the patient's tongue and the electrode array 642. In some embodiments, the locators 602, 606 are elongated crests, trenches, or a combination thereof. In some embodiments, the locators 602 and 606 are integral with the positioning pad 608 and/or the housing 604. In some embodiments, the bottom locator 606 is shaped to accommodate the tip of the patient's tongue. In some embodiments, the top and bottom locators 602, 606 are shaped to accommodate the patient's lips. In some embodiments, the locators 602, 606 include an array of elongated crests, trenches, or a combination thereof and the patient chooses a locator most suitable to his/her anatomy (e.g., to optimize comfort or efficacy of the NINM therapy session).

In some embodiments, the transition region 620 can serve as a top locator 602. The patient can insert the mouthpiece into his/her mouth until the transition region 620 is in contact with his/her upper palate. The transition region 620 can be shaped to substantially conform to the patient's upper palate.

The position of the top locator 602 and the bottom locator 606 can be chosen based on the length of the patient's tongue. For example, for a patient having a tongue length of 4 inches (e.g., from the oropharynx to the tip), the locator may be positioned 2 inches from a posterior boundary 605 of the mouthpiece. In some embodiments, the position of the locator may be chosen based the electrode array 642. For example, the locator may be positioned 3 mm away from the anterior edge of the electrode array 642. In some embodiments, the housing 604 is composed of a plastic material having a hardness of shore 90A. In some embodiments, the positioning pad 608 is a biocompatible material having a hardness of shore 30A. In some embodiments, the top and bottom locators prevent accidental ejection of the mouthpiece 600. In some embodiments, the distance from the posterior electrodes 643 to the posterior boundary is less than 4 mm.

FIGS. 7A-7D show a mouthpiece 700. Mouthpiece 700 includes similar elements as mouthpiece 500 (e.g. mouthpiece 700 includes a housing 704 which is similar to the housing 504 of mouthpiece 500). In some embodiments, the height of the posterior region 724 is sized to accommodate two printed circuit boards. In some embodiments, a positioning pad is included on a bottom portion of transition region 720 or the anterior region 728. Additionally, the operation of the mouthpiece 700 is similar to that described above in reference to FIGS. 5A-5D where similarly referenced elements have the same functionality (e.g., the electrode array 742 has the same functionality as the electrode array 542). In some embodiments, the patient bites down on the positioning pad 708 with his/her front teeth and additionally, bites upward on a positioning pad located on the bottom of the mouthpiece 700 with his/her bottom teeth to secure a position of the mouthpiece. The positioning pad located on the bottom of the mouthpiece 700 can be located between the electrode array 742 and the cable 744.

In some embodiments, the printed circuit board 732 is non-planar. In some embodiments, the printed circuit board 732 is mechanically attached to the housing 704 without the use of screws or fasteners. In some embodiments, the width of the mouthpiece is at least 21 mm to accommodate the average tracheal diameter of a healthy male and additionally, to prevent choking by the patient.

FIGS. 8A-8D show a mouthpiece 800. Mouthpiece 800 includes similar elements as mouthpiece 500 (e.g. mouthpiece 800 includes a housing 804 which is similar to the housing 504 of mouthpiece 500). In some embodiments, a positioning pad is included on a bottom portion of the posterior region 828. The operation of the mouthpiece 800 is similar to that described above in reference to FIGS. 5A-5D where similarly referenced elements have the same functionality (e.g., the electrode array 842 has the same functionality as the electrode array 542).

FIGS. 9A-9D show a mouthpiece 900. Mouthpiece 900 includes similar elements as mouthpiece 500 (e.g. mouthpiece 900 includes a housing 904 which is similar to the housing 504 of mouthpiece 500). The mouthpiece 900 also includes a collection of low profile scallops 909 located within the positioning pad 908. The operation of the mouthpiece 900 is similar to that described above in reference to FIGS. 5A-5D where similarly referenced elements have the same functionality (e.g., the electrode array 942 has the same functionality as the electrode array 542). In some embodiments, the patient can position the mouthpiece using the low profile scallops 909. The patient can bite down on the positioning pad 908 with his/her front teeth, aligning his/her front teeth with one of the low profile scallops 909 shown in FIGS. 9A-9D. For example, a first patient may find that biting down on the most anterior low profile scallop 909 provides the greatest overlap of the tongue with the electrode array 942. A second patient, having a different mouth geometry than the first patient, may find that biting down on the most posterior low profile scallop 909 provides the greatest overlap of the tongue with the electrode array 942. The low profile scallop 909 can be shaped to accommodate the patient's upper teeth. For example, the low profile scallops 909 can have an ovular shape that approximates the shape of at least one tooth bottom. In some embodiments, the scallops 909 provide a corrugated surface to facilitate mechanical stability. In some embodiments, the width of the scallops is slightly smaller than the width of the positioning pad (e.g., the width of the scallops can be 10% less than the width of the positioning pad). In some embodiments, the length of each scallop can be 2 mm. In some embodiments, the length of each scallop is in the range of 1 to 3 mm. In some embodiments, the height of the scallops is in the range of 0.5 mm to 2 mm. In some embodiments, each scallop is spaced apart by at least 2.1 mm, but not more than 10 mm.

FIGS. 10A-10D show a mouthpiece 1000. The mouthpiece 1000 includes similar elements as mouthpiece 500 (e.g. mouthpiece 1000 includes a positioning pad 1008 which is similar to the positioning pad 508 of mouthpiece 500). Additionally, the housing 1004 includes raised regions 1009. The operation of the mouthpiece 1000 is similar to that described above in reference to FIGS. 5A-5D where similarly referenced elements have the same functionality (e.g., the electrode array 1042 has the same functionality as the electrode array 542). In some embodiments, the patient can position the mouthpiece via the raised regions 1009. The raised regions can be shaped to accommodate the patient's fingers. The patient can adjust the position of the mouthpiece 1000 by gripping the raised regions 1009. In some embodiments, the raised regions are spaced apart by about 0.5-1.5 mm.

Figure 11A:
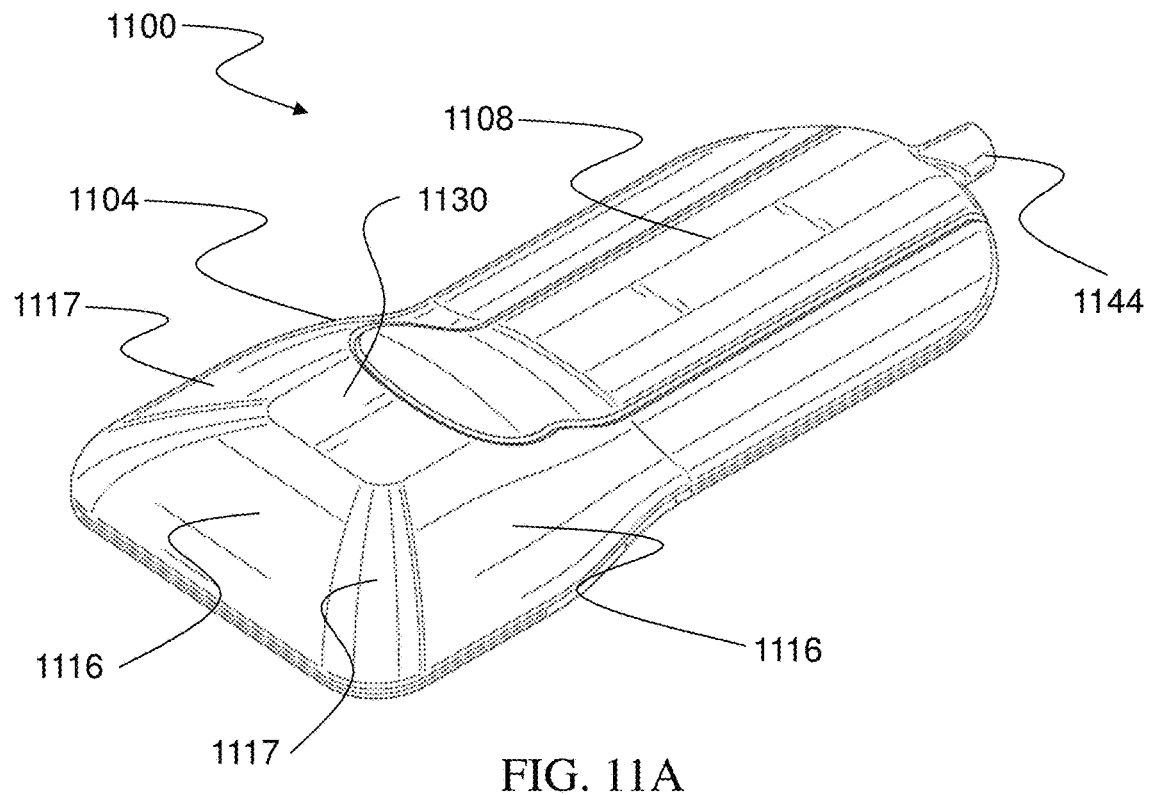
FIG. 11A is a diagram showing an isometric view of a mouthpiece in accordance with an illustrative embodiment of the invention.
Figure 11B:
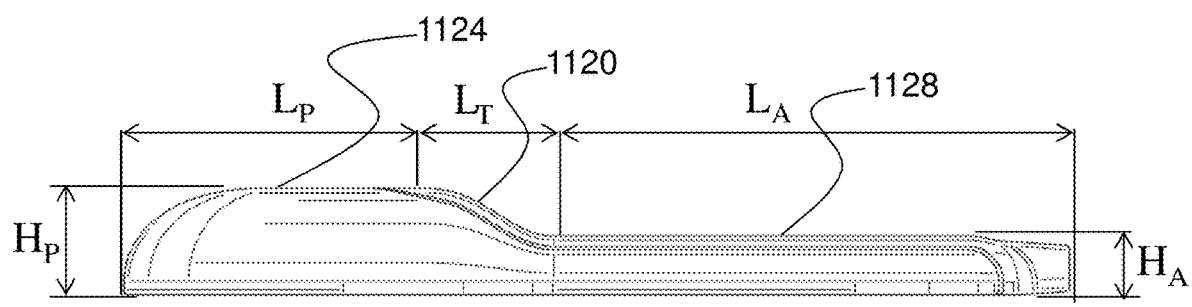
FIG. 11B is a diagram showing a side view of a mouthpiece in accordance with an illustrative embodiment of the invention.
Figure 11C:
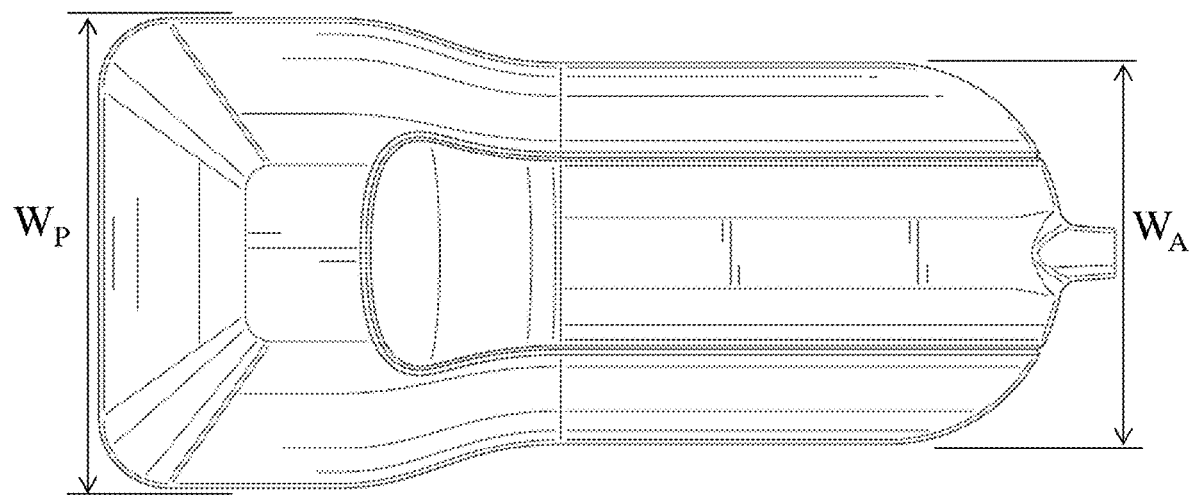
FIG. 11C is a diagram showing a top view of a mouthpiece in accordance with an illustrative embodiment of the invention.
Figure 11D:
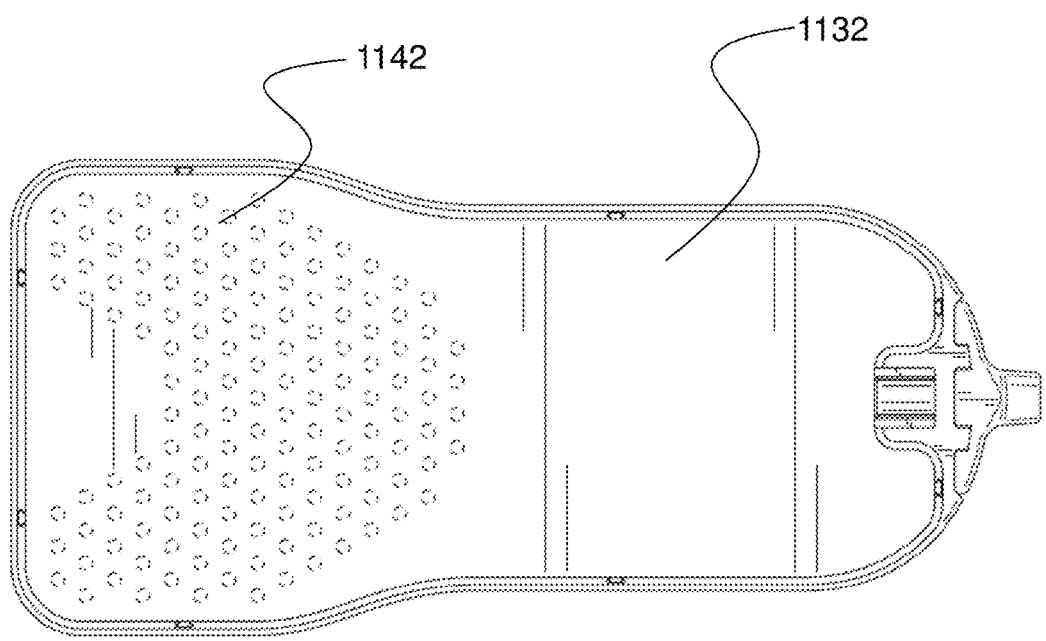
FIG. 11D is a diagram showing a bottom view of a mouthpiece in accordance with an illustrative embodiment of the invention.

FIGS. 11A-11D show a mouthpiece 1100. The mouthpiece 1100 includes a housing 1104, a positioning pad 1108, a transition region 1120, a posterior region 1124, an anterior region 1128, a printed circuit board 1132, internal circuitry, an electrode array 1142, and a cable 1144. The housing 1104 includes chamfered or beveled surfaces 1116, rounds 1117, and a plateau 1130. The mouthpiece 1140 has three regions, a posterior region 1124, a transition region 1120, and an anterior region 1128. The lengths of the posterior region, the transition region, and the anterior region are shown in FIG. 11B as $L_P$, $L_T$, and $L_A$ respectively. The maximum heights of the posterior region and the anterior region are shown in FIG. 11B as $H_P$ and $H_A$ respectively. The maximum widths of the posterior region and the anterior region are shown in FIG. 11C as $W_P$ and $W_A$ respectively. The positioning pad 1108 is attached to the housing 1104 and can form a mesa in an anterior region 1128 of the mouthpiece 1100. The transition region 1120 can smoothly connect the anterior region 1128 with the posterior region 1124. The printed circuit board 1132 is attached to the bottom side of the housing 1104. The internal circuitry is mounted to the top side of the printed circuit board 1132 and is surrounded by the housing 1104. The cable 1144 is in communication with the internal circuitry and the internal circuitry is in communication with the electrode array 1142. The operation of the mouthpiece 1100 is similar to that described above in reference to FIGS. 5A-5D where similarly referenced elements have the same functionality (e.g., the electrode array 1142 has the same functionality as the electrode array 542).

The terminology used herein is for the purpose of describing particular embodiments and is not intended to be limiting of the inventive concepts. It will be understood that, although the terms first, second, third etc. are used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present application.

While the present inventive concepts have been particularly shown and described above with reference to exemplary embodiments thereof, it will be understood by those of ordinary skill in the art, that various changes in form and detail can be made without departing from the spirit and scope of the present inventive concepts described and defined by the following claims.

What is claimed is:

1. A method of placing a mouthpiece in a patient's mouth prior to engaging in a non-invasive neuromodulation therapy session, the method comprising:
    providing a mouthpiece to the patient, the mouthpiece comprising:
        an elongated housing having an anterior region and a posterior region, and a non-planar exterior top surface;
        a positioning pad having an anterior and a posterior region, the positioning pad attached to the top surface of the elongated housing; and
        a first locator traversing a width of a transition region connecting a plateau of the anterior region of the elongated housing to a plateau of the posterior region of the elongated housing, the first locator integral with the top surface of the elongated housing;
    placing the mouthpiece in the patient's mouth; and
    manually adjusting the mouthpiece until the first locator is in contact with the patient's oral cavity.

2. The method of claim 1 wherein the mouthpiece further comprises a second locator traversing an anterior region of a bottom portion of the elongated housing.

3. The method of claim 2, further comprising manually adjusting the mouthpiece until at least one locator is in contact with the tip of the patient's tongue.

4. The method of claim 2, further comprising manually adjusting the mouthpiece until at least one locator is in contact with the patient's lips.

5. The method of claim 2, further comprising manually adjusting the mouthpiece until at least one locator is in contact with the patient's teeth.

6. The method of claim 2 further comprising manually adjusting the mouthpiece until the second locator is in contact with the patient's oral cavity.

7. The method of claim 2 wherein manually adjusting further comprises mechanically coupling the second locator to the patient's lower teeth to secure a position of the mouthpiece within the patient's mouth.

8. The method of claim 7 wherein manually adjusting further comprises mechanically coupling the second locator to at least one of a patient's central incisors, lateral incisors, or canines.

9. The method of claim 2 wherein the second locator comprises an inverted trench, a trench, a contour or a step.

10. The method of claim 1 wherein manually adjusting further comprises preventing the posterior region of the elongated housing, the posterior region of the positioning pad, and the posterior region of the printed circuit board from contacting the patient's tonsils, throat, and circumvallate papillae.

11. The method of claim 1 wherein the first locator comprises an inverted trench, a trench, or a step.

12. The method of claim 1 further comprising manually adjusting the mouthpiece until the patient's bottom teeth contact a printed circuit board mounted to a bottom portion of the elongated housing, the printed circuit board having a plurality of electrodes for delivering subcutaneous local electrical stimulation to the patient's tongue.

13. The method of claim 12 further comprising manually adjusting the mouthpiece until the patient's tongue contacts the plurality of electrodes.

14. A method of placing a mouthpiece in a patient's mouth prior to engaging in a non-invasive neuromodulation therapy session, the method comprising:
providing a mouthpiece to the patient, the mouthpiece comprising:
an elongated housing having an anterior region and a posterior region, the elongated housing having a non-planar exterior top surface;
a positioning pad attached to the top surface of the elongated housing; and
a first locator traversing a width of a transition region connecting a plateau of an anterior region of the positioning pad to a plateau of a posterior region of the positioning pad, the first locator integral with a top surface of the positioning pad;
placing the mouthpiece in the patient's mouth; and
manually adjusting the mouthpiece until the first locator is in contact with the patient's upper teeth to securely position the mouthpiece within the patient's mouth.

15. The method of claim 14 wherein the mouthpiece further comprises a second locator traversing an anterior region of a bottom portion of the elongated housing.

16. The method of claim 15, further comprising manually adjusting the mouthpiece until at least one locator is in contact with the tip of the patient's tongue.

17. The method of claim 15, further comprising manually adjusting the mouthpiece until at least one locator is in contact with the patient's lips.

18. The method of claim 15, further comprising manually adjusting the mouthpiece until at least one locator is in contact with the patient's teeth.

19. The method of claim 15 further comprising manually adjusting the mouthpiece until the second locator is in contact with the patient's anatomy.

20. The method of claim 15 wherein manually adjusting further comprises mechanically coupling the second locator to the patient's lower teeth to secure a position of the mouthpiece within the patient's mouth.

21. The method of claim 15 wherein manually adjusting further comprises mechanically coupling the second locator to at least one of a patient's central incisors, lateral incisors, or canines.

22. The method of claim 15 wherein the second locator comprises an inverted trench, a trench, a contour or a step.

23. The method of claim 14 wherein manually adjusting further comprises preventing the posterior region of the elongated housing, the posterior region of the positioning pad, and the posterior region of the printed circuit board from contacting the patient's tonsils, throat, and circumvallate papillae.

24. The method of claim 14 wherein the first locator comprises an inverted trench, a trench, or a step.

25. The method of claim 14 further comprising manually adjusting the mouthpiece until the patient's bottom teeth contact a printed circuit board mounted to a bottom portion of the elongated housing, the printed circuit board having a plurality of electrodes for delivering subcutaneous local electrical stimulation to the patient's tongue.

26. The method of claim 25 further comprising manually adjusting the mouthpiece until the patient's tongue contacts the plurality of electrodes.

* * * * *